(12) United States Patent
Hastings et al.

(10) Patent No.: US 12,374,070 B2
(45) Date of Patent: Jul. 29, 2025

(54) METHOD AND SYSTEM FOR SURGICAL INSTRUMENTATION SETUP AND USER PREFERENCES

(71) Applicant: Stryker Corporation, Kalamazoo, MI (US)

(72) Inventors: Sean Hastings, Flower Mound, TX (US); Richard A. Beutter, Argyle, TX (US); Andrew Schultz, San Diego, CA (US)

(73) Assignee: Stryker Corporation, Portage, MI (US)

(*) Notice: Subject to any disclaimer, the term of this patent is extended or adjusted under 35 U.S.C. 154(b) by 0 days.

(21) Appl. No.: 18/605,722

(22) Filed: Mar. 14, 2024

(65) Prior Publication Data

US 2024/0273991 A1 Aug. 15, 2024

Related U.S. Application Data

(62) Division of application No. 17/807,701, filed on Jun. 17, 2022, now Pat. No. 11,935,383, which is a
(Continued)

(51) Int. Cl.
*G06V 10/10* (2022.01)
*A61B 5/117* (2016.01)
(Continued)

(52) U.S. Cl.
CPC .............. *G06V 10/10* (2022.01); *A61B 5/117* (2013.01); *G06F 16/50* (2019.01); *G06F 16/583* (2019.01);
(Continued)

(58) Field of Classification Search
CPC ...... G06V 10/10; G06V 10/143; G06V 20/50; G06V 40/10; G06V 20/64; G06V 20/647;
(Continued)

(56) References Cited

U.S. PATENT DOCUMENTS 5,376,796 A 12/1994 Chan
5,432,703 A 7/1995 Clynch
(Continued)

FOREIGN PATENT DOCUMENTS

CN 202724392 U 2/2013
CN 204618192 U 9/2015
(Continued)

OTHER PUBLICATIONS

Abdelmoghith et al.. "IoT-Based Healthcare Monitoring System: Bedsores Prevention," 2020 Fourth World Conference on Smart Trends in Systems, Security and Sustainability (WorldS4), Jul. 27-28, 2020, London, United Kingdom; pp. 64-69.
(Continued)

*Primary Examiner* — Thomas Randazzo
(74) *Attorney, Agent, or Firm* — Morrison & Foerster LLP

(57) ABSTRACT

A method of sterilizing an operating room comprises, at a computing system, capturing a first image of the operating room by at least one camera; determining that no people are present in the operating room based on analysis of the first image; and in response to determining that no people are present in the operating room, controlling an ultraviolet room sterilization system to sterilize at least a portion of the operating room.

27 Claims, 14 Drawing Sheets

Related U.S. Application Data division of application No. 16/735,521, filed on Jan. 6, 2020, now Pat. No. 11,367,304, which is a division of application No. 15/190,636, filed on Jun. 23, 2016, now Pat. No. 10,528,840.

(60) Provisional application No. 62/183,995, filed on Jun. 24, 2015.

(51) Int. Cl.
| | |
|---|---|
| *G06F 16/50* | (2019.01) |
| *G06F 16/583* | (2019.01) |
| *G06T 7/00* | (2017.01) |
| *G06V 10/143* | (2022.01) |
| *G06V 20/50* | (2022.01) |
| *G06V 40/10* | (2022.01) |
| *G08B 21/00* | (2006.01) |
| *G08B 21/04* | (2006.01) |
| *G09B 5/02* | (2006.01) |
| *G16H 40/63* | (2018.01) |
| *A61B 34/10* | (2016.01) |
| *G06V 20/64* | (2022.01) |

(52) U.S. Cl.
CPC ............ *G06T 7/001* (2013.01); *G06V 10/143* (2022.01); *G06V 20/50* (2022.01); *G06V 40/10* (2022.01); *G08B 21/00* (2013.01); *G08B 21/0476* (2013.01); *G09B 5/02* (2013.01); *G16H 40/63* (2018.01); *A61B 34/10* (2016.02); *A61B 2562/08* (2013.01); *G06T 2207/10036* (2013.01); *G06T 2207/30196* (2013.01); *G06V 20/64* (2022.01); *G06V 20/647* (2022.01)

(58) Field of Classification Search
CPC ..... A61B 5/117; A61B 34/10; A61B 2562/08; A61B 2034/2065; A61B 2090/306; A61B 2090/309; A61B 2090/3614; G06F 16/50; G06F 16/583; G06T 7/001; G06T 2207/10036; G06T 2207/30196; G08B 21/00; G08B 21/0476; G09B 5/02; G16H 40/63

See application file for complete search history.

(56) References Cited

U.S. PATENT DOCUMENTS

| | | | |
|---|---|---|---|
| 5,477,371 A | 12/1995 | Shafir | |
| 5,627,586 A | 5/1997 | Yamasaki | |
| 6,044,288 A | 3/2000 | Wake | |
| 6,119,033 A | 9/2000 | Spigelman | |
| 6,223,137 B1 | 4/2001 | Mccay | |
| 6,442,419 B1 | 8/2002 | Chu | |
| 6,486,778 B2 | 11/2002 | Mahler | |
| 6,987,448 B2 | 1/2006 | Catton et al. | |
| 7,248,933 B2 | 7/2007 | Wildman | |
| 7,378,975 B1 | 5/2008 | Smith et al. | |
| 7,457,804 B2 | 11/2008 | Uber, III | |
| 7,768,414 B2 | 8/2010 | Abel et al. | |
| 7,783,676 B2 | 8/2010 | Lim | |
| 8,231,664 B2 | 7/2012 | Kulstad et al. | |
| 8,426,813 B2* | 4/2013 | Furry ............... | G01N 21/3518 250/330 |
| 8,452,615 B2 | 5/2013 | Abri | |
| 8,754,945 B2 | 6/2014 | Lee | |
| 9,143,843 B2* | 9/2015 | De Luca ............... | H04Q 9/02 |
| 9,183,602 B2 | 11/2015 | Olarte | |
| 9,280,884 B1 | 3/2016 | Schultz et al. | |
| 9,305,218 B2 | 4/2016 | Lewis | |
| 9,442,070 B1 | 9/2016 | Hug et al. | |
| 9,452,339 B1 | 9/2016 | Shah | |
| 9,505,494 B1* | 11/2016 | Marlow ............... | G05D 1/0011 |
| 9,693,891 B2 | 7/2017 | Macintyre-ellis et al. | |
| 9,807,475 B2 | 10/2017 | Subiry | |
| 9,908,239 B1* | 3/2018 | O'Brien ............... | B25J 5/007 |
| 9,956,113 B2 | 5/2018 | Santa Maria et al. | |
| 10,020,075 B2 | 7/2018 | Perlman et al. | |
| 10,269,454 B2 | 4/2019 | Hanning et al. | |
| 10,600,204 B1 | 3/2020 | Rush et al. | |
| 10,631,783 B2 | 4/2020 | Persson | |
| 10,688,269 B2 | 6/2020 | Scharmer et al. | |
| 10,729,502 B1 | 8/2020 | Wolf et al. | |
| 10,859,474 B2 | 12/2020 | Chou et al. | |
| 11,040,155 B2 | 6/2021 | Hong | |
| 11,051,751 B2 | 7/2021 | Larson et al. | |
| 11,076,778 B1 | 8/2021 | Abbas | |
| 2003/0216836 A1 | 11/2003 | Treat | |
| 2004/0186683 A1 | 9/2004 | Farber | |
| 2006/0234175 A1 | 10/2006 | Bridgwater et al. | |
| 2006/0243720 A1 | 11/2006 | Koch et al. | |
| 2007/0027403 A1 | 2/2007 | Kosted | |
| 2007/0239482 A1 | 10/2007 | Finn | |
| 2008/0281301 A1 | 11/2008 | Deboer et al. | |
| 2008/0312963 A1 | 12/2008 | Reiner | |
| 2009/0300507 A1 | 12/2009 | Raghavan | |
| 2009/0323121 A1 | 12/2009 | Valkenburg | |
| 2009/0326336 A1 | 12/2009 | Lemke | |
| 2010/0225746 A1 | 9/2010 | Shpunt | |
| 2010/0290698 A1 | 11/2010 | Arieli | |
| 2012/0014562 A1 | 1/2012 | Berkovich | |
| 2012/0078144 A1 | 3/2012 | Sinykin | |
| 2012/0083652 A1 | 4/2012 | Langlois et al. | |
| 2012/0140068 A1 | 6/2012 | Monroe | |
| 2012/0146789 A1* | 6/2012 | De Luca ............... | G08B 21/24 382/103 |
| 2012/0146792 A1* | 6/2012 | De Luca ............... | G08B 21/22 340/568.1 |
| 2012/0268280 A1 | 10/2012 | Hatch et al. | |
| 2013/0247921 A1 | 9/2013 | Dye et al. | |
| 2013/0267779 A1 | 10/2013 | Woolford | |
| 2013/0285947 A1* | 10/2013 | Hunter ............... | G16H 10/20 345/173 |
| 2014/0006943 A1 | 1/2014 | Robbins et al. | |
| 2014/0036110 A1 | 2/2014 | Ragozin | |
| 2014/0039351 A1 | 2/2014 | Mix et al. | |
| 2014/0267770 A1 | 9/2014 | Gervautz | |
| 2014/0276056 A1 | 9/2014 | Ohta et al. | |
| 2014/0285432 A1 | 9/2014 | Guez et al. | |
| 2014/0358044 A1 | 12/2014 | Kirwan et al. | |
| 2015/0086072 A1 | 3/2015 | Kompalli et al. | |
| 2015/0149330 A1 | 5/2015 | Sweeney | |
| 2015/0190202 A1 | 7/2015 | Weinert | |
| 2015/0288924 A1 | 10/2015 | Liu et al. | |
| 2015/0302157 A1 | 10/2015 | Collar et al. | |
| 2015/0310718 A1 | 10/2015 | Wilson et al. | |
| 2015/0317068 A1 | 11/2015 | Marka | |
| 2016/0061794 A1 | 3/2016 | Schultz et al. | |
| 2016/0061795 A1 | 3/2016 | Schultz et al. | |
| 2016/0078307 A1 | 3/2016 | Pawlik | |
| 2016/0085922 A1 | 3/2016 | Sweeney | |
| 2016/0103810 A1 | 4/2016 | Hanning | |
| 2016/0120691 A1 | 5/2016 | Kirwan et al. | |
| 2016/0203699 A1* | 7/2016 | Mulhern ............... | G06V 20/52 340/573.1 |
| 2016/0220323 A1 | 8/2016 | Forrest | |
| 2016/0224999 A1 | 8/2016 | Mukherjee et al. | |
| 2016/0239718 A1 | 8/2016 | Korenwaitz | |
| 2016/0239795 A1 | 8/2016 | Burch, V | |
| 2016/0314258 A1 | 10/2016 | Kusens | |
| 2016/0379504 A1 | 12/2016 | Bailey et al. | |
| 2017/0140113 A1 | 5/2017 | Hunter et al. | |
| 2017/0185864 A1 | 6/2017 | Nicoara | |
| 2017/0231577 A1 | 8/2017 | Ben Shalom et al. | |
| 2017/0281073 A1 | 10/2017 | Drennan et al. | |
| 2018/0011983 A1 | 1/2018 | Zuhars et al. | |
| 2018/0052072 A1 | 2/2018 | Koh | |
| 2018/0071137 A1 | 3/2018 | Kuras et al. | |
| 2018/0243025 A1 | 8/2018 | Smits et al. | |
| 2018/0250484 A1* | 9/2018 | McCormick ............... | A61B 1/05 |
| 2019/0104982 A1 | 4/2019 | Dunn et al. | |

(56) References Cited

U.S. PATENT DOCUMENTS

| | | |
|---|---|---|
| 2019/0307405 A1 | 10/2019 | Terry et al. |
| 2019/0311599 A1 | 10/2019 | Jensen et al. |
| 2019/0328598 A1 | 10/2019 | Mangiardi |
| 2019/0374375 A1 | 12/2019 | Mcgregor et al. |
| 2019/0374387 A1 | 12/2019 | Ribble et al. |
| 2020/0113488 A1 | 4/2020 | Al-ali et al. |
| 2020/0155059 A1 | 5/2020 | Kayser et al. |
| 2020/0245950 A1 | 8/2020 | Liang et al. |
| 2020/0246180 A1 | 8/2020 | Liang et al. |
| 2020/0405217 A1 | 12/2020 | Jayaraman et al. |
| 2021/0038084 A1 | 2/2021 | Dion et al. |
| 2024/0273991 A1 | 8/2024 | Hastings |

FOREIGN PATENT DOCUMENTS

| | | |
|---|---|---|
| CN | 111352378 A | 6/2020 |
| CN | 211432863 U | 9/2020 |
| CN | 112426266 A | 3/2021 |
| DE | 4339379 A1 | 5/1995 |
| EP | 2143090 A1 | 9/2007 |
| EP | 2391317 A1 | 8/2010 |
| EP | 3556318 A1 | 10/2019 |
| WO | 2004/014246 A1 | 2/2004 |
| WO | 2007/106040 A1 | 9/2007 |
| WO | 2010/086740 A1 | 8/2010 |
| WO | 2013/104420 A1 | 7/2013 |
| WO | 2013/186160 A1 | 12/2013 |
| WO | 2015/092627 A1 | 6/2015 |
| WO | 2017/183602 A1 | 10/2017 |
| WO | 2020/031147 A1 | 2/2020 |
| WO | 2020/165918 A1 | 8/2020 |
| WO | 2020/243527 A1 | 12/2020 |
| WO | 2020/264140 A1 | 12/2020 |
| WO | 2021/021609 A1 | 2/2021 |
| WO | 2021/096996 A1 | 5/2021 |
| WO | 2021/097367 A1 | 5/2021 |

OTHER PUBLICATIONS

Anderson et al. (Jun. 2014). "Strategies to Prevent Surgical Site Infections in Acute Care Hospitals: 2014 Update," Infection Control and Hospital Epidemiology 35(6): 605-627.

Association of Surgical Technologists. (Apr. 10, 2015). "AST Guidelines for Best Practice in Maintaining Normothermia in the Perioperative Patient," 32 pages.

Bailey et al., U.S. Notice of Allowance and Fee(s) Due dated Aug. 26, 2019, directed to U.S. Appl. No. 15/190,636; 10 pages.

Bailey et al., U.S. Office Action dated Apr. 26, 2018, directed to U.S. Appl. No. 15/190,636; 27 pages.

Bailey et al., U.S. Office Action dated Dec. 17, 2018, directed to U.S. Appl. No. 15/190,636; 24 pages.

Bailey et al., U.S. Office Action dated Jun. 7, 2017, directed to U.S. Appl. No. 15/190,636; 21 pages.

Bailey et al., U.S. Office Action dated Nov. 17, 2017 directed to U.S. Appl. No. 15/190,636; 24 pages.

Bailey et al., U.S. Restriction Requirement dated Jan. 25, 2017, directed to U.S. Appl. No. 15/190,636; 6 pages.

Barker et al. (1997). "Anaesthetic pollution. Potential sources, their identification and control," Anaesthesia 52:1077-1083.

Berrios-Torres et al., (2017). "Centers for Disease Control and Prevention Guideline for the Prevention of Surgical Site Infection, 2017," JAMA Surgery 152(8): 784-791.

Chang et al. (1997). "Exposure of Anesthesiologists to Nitrous Oxide during Pediatric Anesthesia," Industrial Health 35(1):112-118.

Frank et al. (Feb. 1999). "Temperature Monitoring Practices During Regional Anesthesia," International Anesthesia Research Society 88(2): 373-377.

GenTherm. (2021). "Normothermia Astopad™," located at https://gentherm.com/index.php/en/medical/ normothermia/astopad; 3 pages.

Gilly et al. (Nov. 1991). "Anesthetic gas contamination in the operating room—an unsolved problem? Results of our own studies," Anaesthesist 40(11):629-637.

Hastings et al., U.S. Notice of Allowance and Fee(s) due mailed Feb. 16, 2022, directed to U.S. Appl. No. 16/735,521; 10 pages.

Hastings et al., U.S. Notice of Allowance and Fee(s) Due mailed Nov. 9, 2023, directed to U.S. Appl. No. 17/807,701; 10 pages.

Hastings et al., U.S. Office Action dated Apr. 27, 2021, directed to U.S. Appl. No. 16/735,521; 10 pages.

Hastings et al., U.S. Office Action dated Sep. 9, 2021, directed to U.S. Appl. No. 16/735,521; 14 pages.

Hsiao et al. (2016). "Body posture recognition and turning recording system for the care of bed bound patients," Technology and Health Care 24: S307-S312.

Kanmura et al. (Mar. 1999). "Causes of Nitrous Oxide Contamination in Operating Rooms," Anesthesiology 90(3):693-696.

Kole. (Oct. 1990). "Environmental and occupational hazards of anesthesia workplace," AANA J 58(5):327-331.

Monroy et al. (Jun. 2020). "Fuzzy monitoring of in-bed postural changes for the prevention of pressure ulcers using inertial sensors attached to clothing," Journal of Biomedical Informatics 107: 1-12.

Nararoff et al. (Apr. 2021). "Tracking Bedridden Patient Positions Using Micro-Doppler Signature," IEEE Sensors Letters 5(4): 1-4.

Omni™. (Nov. 12, 2021) "Omni™ Suite Overview Video," located at https://zimmerbiomet.tv/videos/2521. (9 pages).

OSHA. (Jul. 20, 1999). "Anesthetic Gases: Guidelines for Workplace Exposures," located at https://www.osha.gov/waste-anesthetic-gases/workplace-exposures-guidelines, 78 pages.

Pickham et al. (2016). "Evaluating optimal patient-turning procedures for reducing hospital acquired pressure ulcers (LS-HAPU): study protocol for a randomized controlled trial," Trials 17(190.): 1-8.

Sen et al. "Wireless Sensor Patch Suitable for Continuous Monitoring of Contact Pressure in a Clinical Setting," 2018 16th IEEE International New Circuits and Systems Conference (NEWCAS), Jun. 24-27, 2018, Montréal, Canada; pp. 91-95.

Sessler, D. (Aug. 2008). "Temperature Monitoring and Perioperative Thermoregulation," Anesthesiology 109(2): 318-338.

Özelsel et al. (2018). "Elevated Waste Anaesthetic Gas Concentration in the Paediatric Post-Anaesthesia Care Unit," Turk J Anaesthesiol Reanim 46(5):362-366.

\* cited by examiner

METHOD AND SYSTEM FOR SURGICAL INSTRUMENTATION SETUP AND USER PREFERENCES

CROSS-REFERENCE TO RELATED APPLICATIONS

This application is a divisional of U.S. patent application Ser. No. 17/807,701, filed Jun. 17, 2022, which is a divisional of U.S. patent application Ser. No. 16/735,521, filed Jan. 6, 2020, now U.S. Pat. No. 11,367,304, which is a divisional of U.S. patent application Ser. No. 15/190,636, filed Jun. 23, 2016, now U.S. Pat. No. 10,528,840, which claims the benefit of U.S. Provisional Application No. 62/183,995, filed Jun. 24, 2015, the entire contents of each of which are incorporated herein by reference.

FIELD OF THE INVENTION

The present invention relates to a method of setting up a medical care area, such as an operating room, and in particular to a method of arranging medical or surgical devices in an operating room.

BACKGROUND OF THE INVENTION

Current methods for set up of medical care areas, such as an operative theater, include arranging the medical care area or operative theater according to the instructions on a surgical preference card. For each procedure that a surgeon performs, a separate preference card is maintained. The surgical preference cards outline a variety of items, including surgical equipment preference and layout, patient positioning, and surgical video equipment setup. At a large hospital, where there are many surgeons and many procedures to be performed, thousands of surgical preference cards must be arranged, tracked and utilized.

Surgical preference cards have become extremely important as hospitals push toward more efficient workflows and strive to complete more surgeries in any given day. The surgical preference cards help the surgical staff avoid time consuming (and costly) situations wherein the equipment is improperly arranged in the operative theater prior to surgery and/or essential equipment is missing. Many products have recently been employed to automate management, creation and use of the surgical preference cards including digitizing the surgical preference cards.

A fast, easy and reliable method of arranging the medical or surgical devices in a medical care area is desired.

SUMMARY OF THE INVENTION

The present invention, according to one aspect, is directed to a method of setting up an operating room including placing at least one surgical device on at least one surface in the operating room, capturing an image of the at least one surgical device with a camera, comparing actual attributes of the at least one surgical device determined using the image captured by the camera with desired attributes of the at least one surgical device stored in a digital preference storage using a computer system, and issuing instruction information of the at least one surgical device in the operating room, the instruction information being dependent on results of the step of comparing.

Yet another aspect of the present invention is to provide a method of arranging a medical care area. The method includes placing at least one medical or surgical device in the medical care area, capturing an image of the at least one medical or surgical device with a camera, with the image including at least one actual attribute of the at least one medical or surgical device, storing at least one desired attribute of the at least one medical or surgical device in a digital preference storage using a computer system, comparing the at least one actual attribute of the at least one medical or surgical device using the image captured by the camera with the at least one desired attribute stored in the digital preference storage, and issuing instruction information in the medical care area to personnel responsible for arranging the medical care area, the instruction information including at least one of: the number present, the style, the location and the orientation of the at least one medical or surgical device located in the medical care area.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

The specific devices and processes illustrated in the attached drawings, and described in the following specification are simply exemplary embodiments of the inventive concepts. Hence, specific dimensions and other physical characteristics relating to the embodiments disclosed herein are not to be considered as limiting.

DETAILED DESCRIPTION

For purposes of description herein, it is to be understood that the invention may assume various alternative orientations, except where expressly specified to the contrary. It is also to be understood that the specific devices and processes illustrated in the attached drawings, and described in the following specification are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
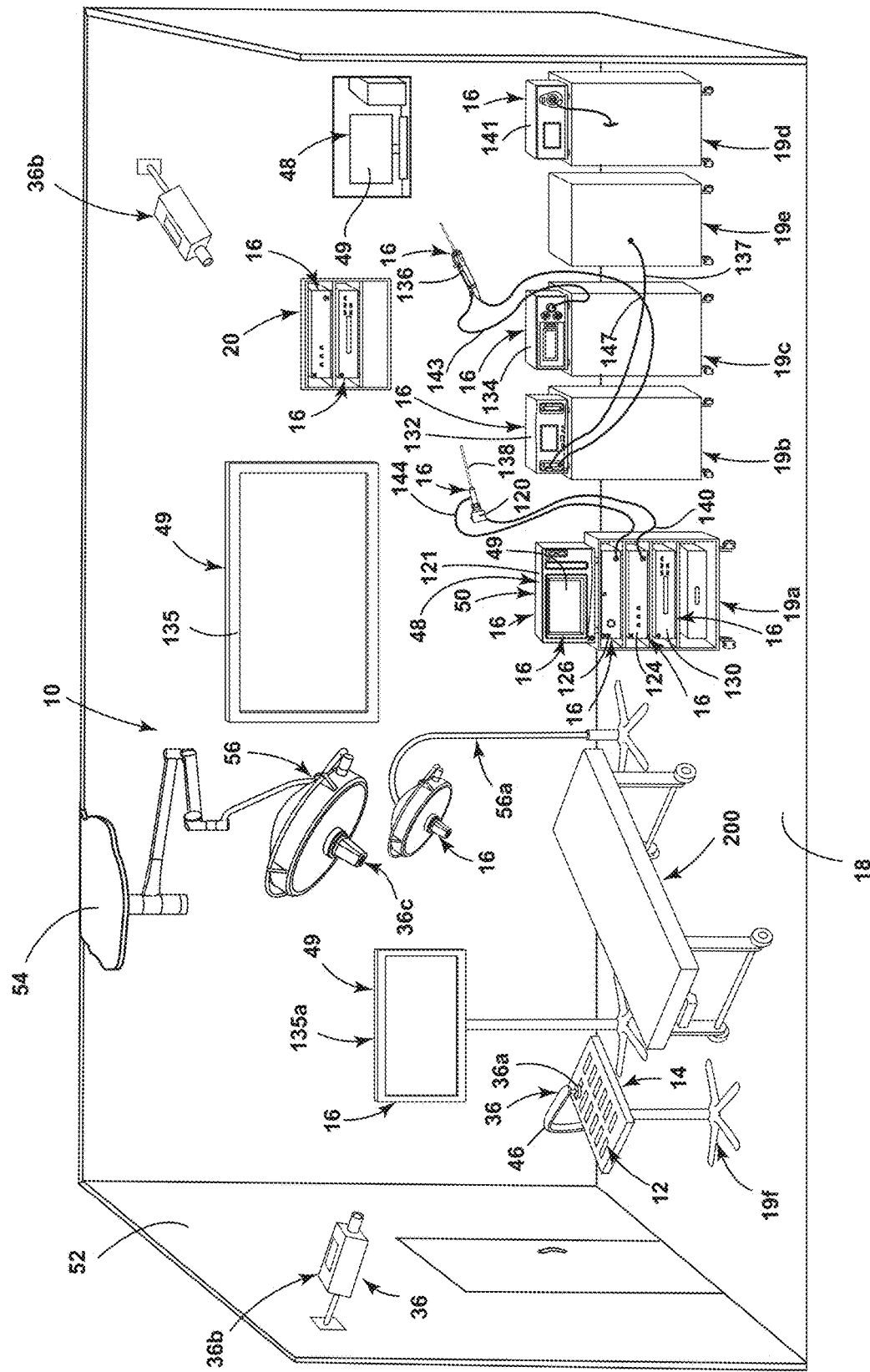
FIG. 1 is a perspective view of an operating room illustrating examples of surgical devices used in a method of the present invention.

FIG. 1 depicts a perspective view of a medical care area 10, which in the illustrated embodiment is depicted as an operating room, according to one embodiment of the invention. In the illustrated example, the operating room 10 includes surgical devices placed throughout the operating room 10. The surgical devices can include surgical instruments 12 positioned on a table 14 (stationary or portable) and surgical equipment 16 positioned on a floor 18, on a portable cart 19a, 19b, 19c, 19d, 19e and/or on shelving 20 in the operating room 10. An aspect of the present invention is to ensure that the surgical devices are properly placed and present in the operating room 10 by capturing images of the surgical devices using optical recognition programs to recognize the presence of the surgical devices and indicating that all surgical devices are properly placed and present or that changes need to be made to the surgical devices (e.g., changing the location of one or more of the surgical devices, adding more surgical devices and/or removing some of the surgical devices).

Figure 2:
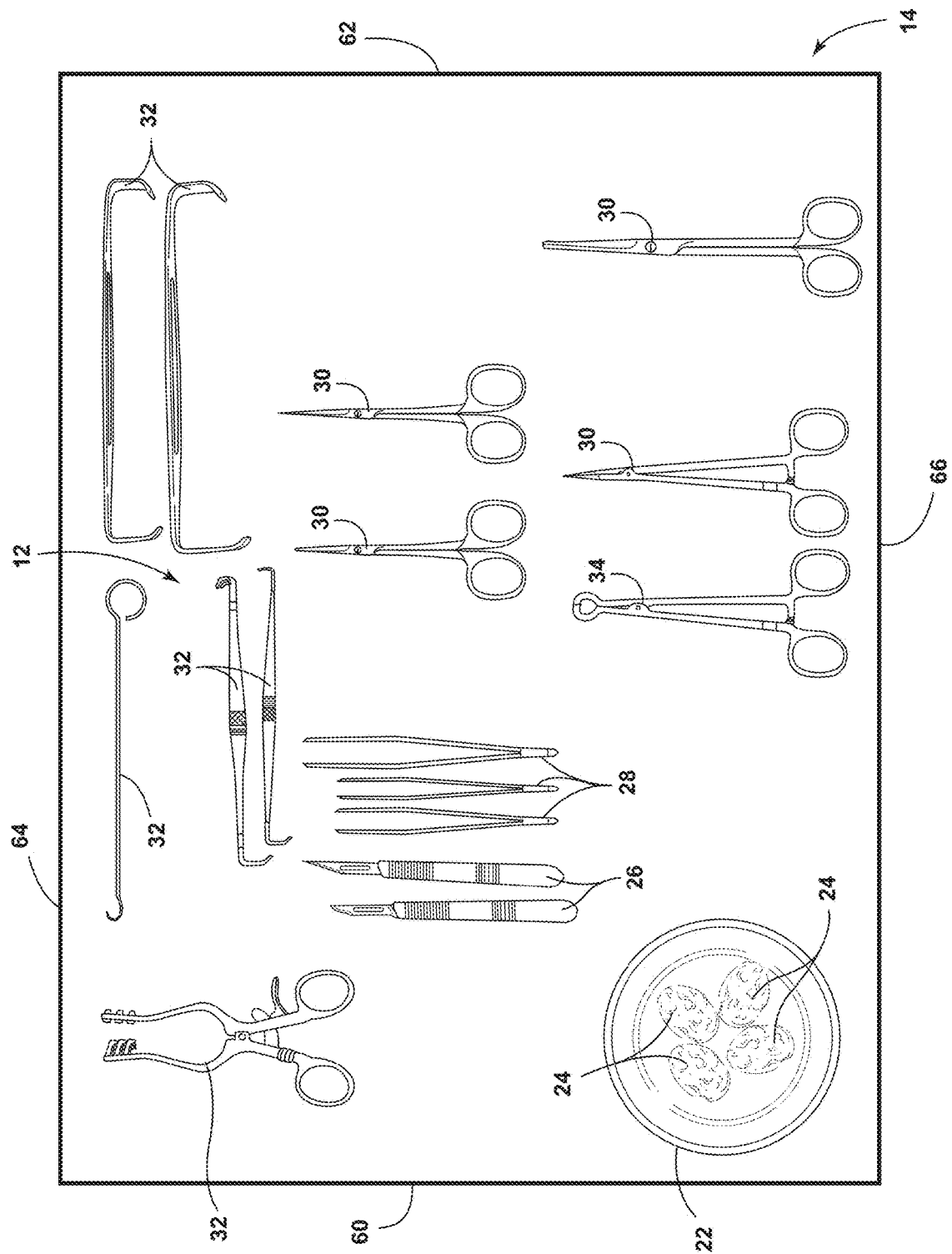
FIG. 2 illustrates a top view of an example of surgical instruments on a surface used in the method of the present invention.

FIG. 2 illustrates a plurality of surgical instruments 12 on the table 14 (or on a tray on the table 14). The surgical instruments 12 can be any specially designed tool or device for performing specific actions of carrying out desired effects during a surgery or operation, such as modifying biological tissue, or to provide access for viewing biological tissue. Examples of surgical instruments 12 include graspers, such as forceps, clamps and occluders for blood vessels and other organs, retractors used to spread open skin, ribs and other tissue, distractors, positioners and stereotactic devices, mechanical cutters (scalpels, lancets, drill bits, rasps, trocars, Ligasure, Harmonic scalpel, rongeurs etc.), dilators and specula for access to narrow passages or incisions, suction tips and tubes for removal of bodily fluids, sealing devices, such as surgical staplers, irrigation and injection needles, tips and tubes for introducing fluid, powered devices, such as drills, scopes and probes, including fiber optic endoscopes and tactile probes, carriers and appliers for optical, electronic and mechanical devices, ultrasound tissue disruptors, cryotomes and cutting laser guides, sponges, and measurement devices, such as rulers and calipers. The above list is not exhaustive and is for illustrative purposes only. In the illustrated example of FIG. 2, the surgical instruments 12 on the table 14 include a bowl 22 holding sponges 24, a plurality of scalpels 26, a plurality of forceps 28, a plurality of scissors 30, a plurality of retractors 32, and a sponge clamp 34.

Figure 3:
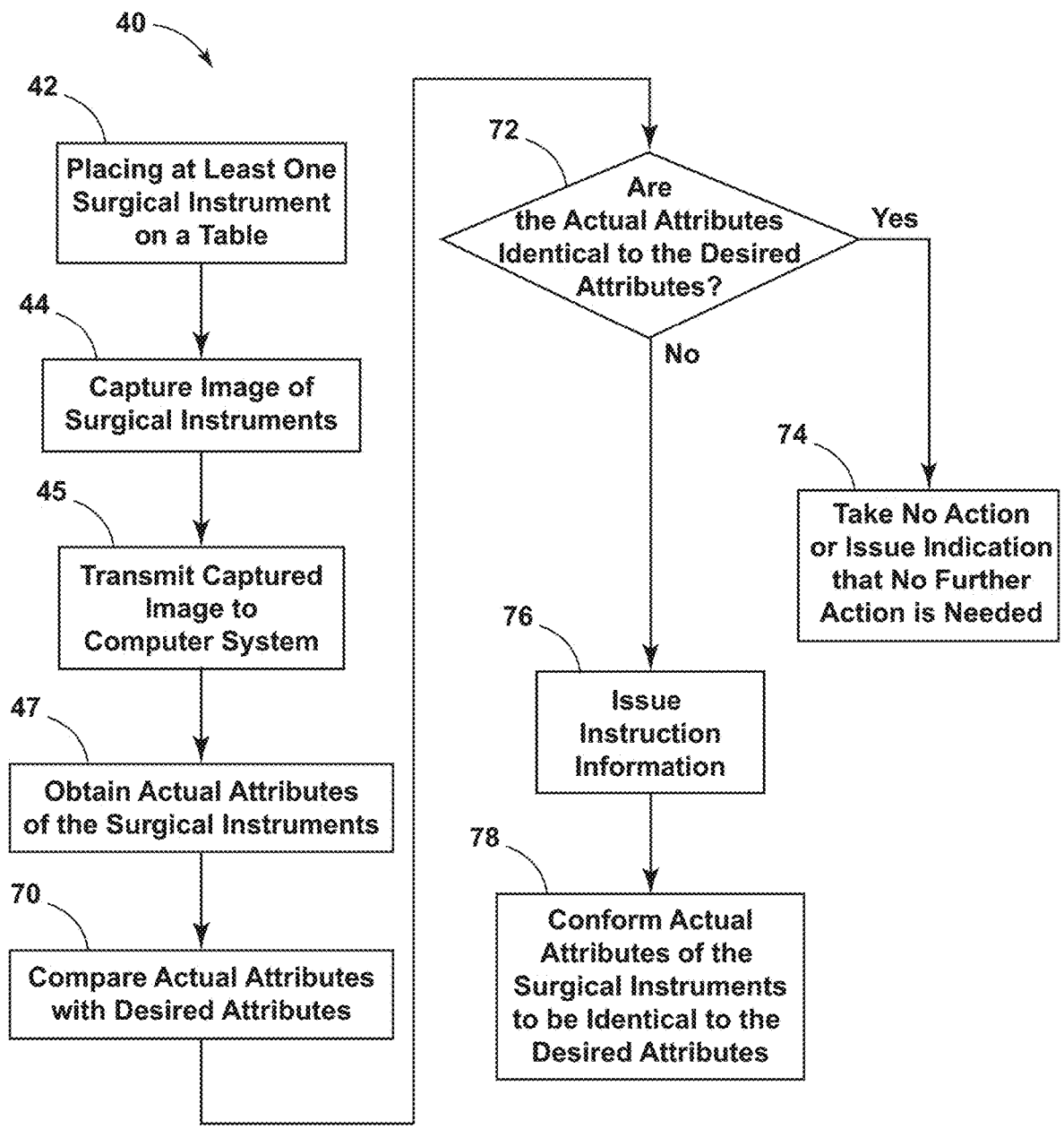
FIG. 3 illustrates a method of properly locating the surgical instruments.

An aspect of the present invention is to ensure that the proper surgical instruments 12 are located on the table 14 and in the proper position on the table 14 according to preferences of particular medical personnel (e.g., a surgeon) or according to a particular procedure being performed. FIG. 3 illustrates a method 40 of properly locating the surgical instruments 12. In a first step of the method 40, at least one surgical instrument 12 is placed on the table 14 at step 42. Typically, a plurality of the surgical instruments 12 are placed on the table 14 (see, for example, FIG. 2). After the surgical instruments 12 are placed on the table 14, a camera 36 captures an image of the surgical instruments 12 on the table 14 at step 44. The camera 36 can be a table camera 36a fixed to the table 14 by a bracket 46 and pointed at the table 14 to be able to capture an image of the entire table 14 and all surgical instruments 12 thereon. The camera 36 could also or alternatively be a room camera 36b fixed to walls 52 or a ceiling 54 of the room 10 (e.g., a room camera 36b as shown or a camera 36c in an overhead light 56). It is contemplated that the camera 36 could be a high definition camera, a 360° camera and/or a wide-angle camera. The image of the surgical instruments 12 captured by the camera 36 at step 44 is then transmitted to a computer system 48 for analysis at step 45. The computer system 48 (e.g., desktop or laptop computer) can be located in the room 10 (or elsewhere) or can be an image and video capture and recording device 50 as discussed in more detail below. The computer system 48 includes one or more processors or other similar control devices as well as one or more memory devices. The processor controls the overall operation of the computer system 48 and can include hardwired circuitry, programmable circuitry that executes software, or a combination thereof. The processor may, for example, execute software stored in the memory device. The processor may include, for example, one or more general- or special-purpose programmable microprocessors and/or microcontrollers, application specific integrated circuits (ASICs), programmable logic devices (PLDs), programmable gate arrays (PGAs), or the like. The memory device may include any combination of one or more random access memories (RAMs), read-only memories (ROMs) (which may be programmable), flash memory, and/or other similar storage devices. It is contemplated that the camera 36 could be a camera of a tablet computer and the computer system 48 can be incorporated into the tablet computer. The camera 36 can transmit the image to the computer system 48 wirelessly or via a wired system.

After the computer system 48 receives the image of the surgical instruments 12 captured by the camera 36 at step 45, the computer system 48 obtains actual attributes of the surgical instruments 12 at step 47. The actual attributes of the surgical instruments 12 can include the number of each of the particular surgical instruments 12, the style of the surgical instruments 12, the brand of the surgical instruments 12, the location/orientation of the surgical instruments 12 on the table 14 and/or the presence of the surgical instruments 12. It is contemplated that other actual attributes of the surgical instruments 12 could be found. The actual attributes of the surgical instruments 12 can be found using an image recognition algorithm (e.g., using Haar Cascade classifier). Such image recognition algorithms are well known to those skilled in the art. It is also contemplated that the surgical instruments 12 could include a linear or matrix bar code thereon for determining the actual attributes of the surgical instruments 12. It is further contemplated that the surgical instruments 12 could include indicators thereon for assisting in determining the actual attributes of the surgical instruments 12. For example, two surgical instruments 12 may have the same outside configuration, but have different internal parts on components. In such a situation, the different surgical instruments 12 could each include a different exterior visual indicator (e.g., a modulated infrared or other spectrum beacon, different colors, or different linear or matrix bar code thereon) to allow the computer system 48 to properly identify the surgical instrument 12.

For the example of the surgical instruments 12 on the table 14 illustrated in FIG. 2, the actual attributes of the surgical instruments 12 could include the number of sponges 24 (4), scalpels 26 (2), forceps 28 (3), scissors 30 (4), retractors 32 (6) and sponge clamps 34 (1). The actual attributes of the surgical instruments 12 could further include the style of the surgical instruments 12. For example, the computer system 48 can determine the style of the retractors 32 (1 Cushing decompression retractor, 2 Senn retractors, 2 army navy retractors and 1 Weitlander retractor in the example of FIG. 2) and/or the brand (i.e., manufacturer) of the retractors 32. The actual attributes of the surgical instruments 12 could also include the location of the surgical instruments 12. For example, the computer system 48 can determine the location (including orientation) of the surgical instruments 12 on the table 14 (e.g., relative to a left side edge 60, a right side edge 62, a top edge 64 and bottom edge 66 of the table 14 as illustrated in FIG. 2). Moreover, actual attributes of the surgical instruments 12 could further be a determination of the presence of the surgical instruments 12. For example, the computer system 48 can determine that the table 14 includes sponges 24, scalpels 26, forceps 28, scissors 30, retractors 32 and sponge clamps 34. The actual attributes can be a combination of any of the above-noted actual attributes.

After the computer system 48 obtains actual attributes of the surgical instruments 12 at step 47, the computer system 48 compares the actual attributes of the surgical instruments 12 with desired attributes of the surgical instruments 12 at step 70. The desired attributes of the surgical instruments 12 are stored in a digital preference storage. The digital preference storage can be saved in the computer system 48 or retrievable by the computer system 48. It is contemplated that the computer system 48 may process information and include the digital preference storage on the Internet or other type of wide area network (WAN), a local area network (LAN), a corporate intranet, any other type of network, a combination of such networks, or can be stored in cloud storage retrievable through a network interface of the computer system 48. For example, the digital preference storage can be located in existing hospital IT systems (e.g., a hospital's electronic medical record (EMR)).

In the method 40 of properly locating the surgical instruments 12, if the actual attributes of the surgical instruments 12 are identical to the desired attributes as determined at decision step 72, no further action is taken or the computer system 48 issues instruction information indicating that no further action is needed at step 74. The computer system 48 can issue an indication that no further action is needed using any visual and/or audio notification. For example, the computer system 48 can issue an "OK" message on an associated or attached display or monitor 49, can flash a green light, can issue audio stating that all of the surgical instruments 12 are proper and in the correct location or any combination of the above.

Figure 4A:
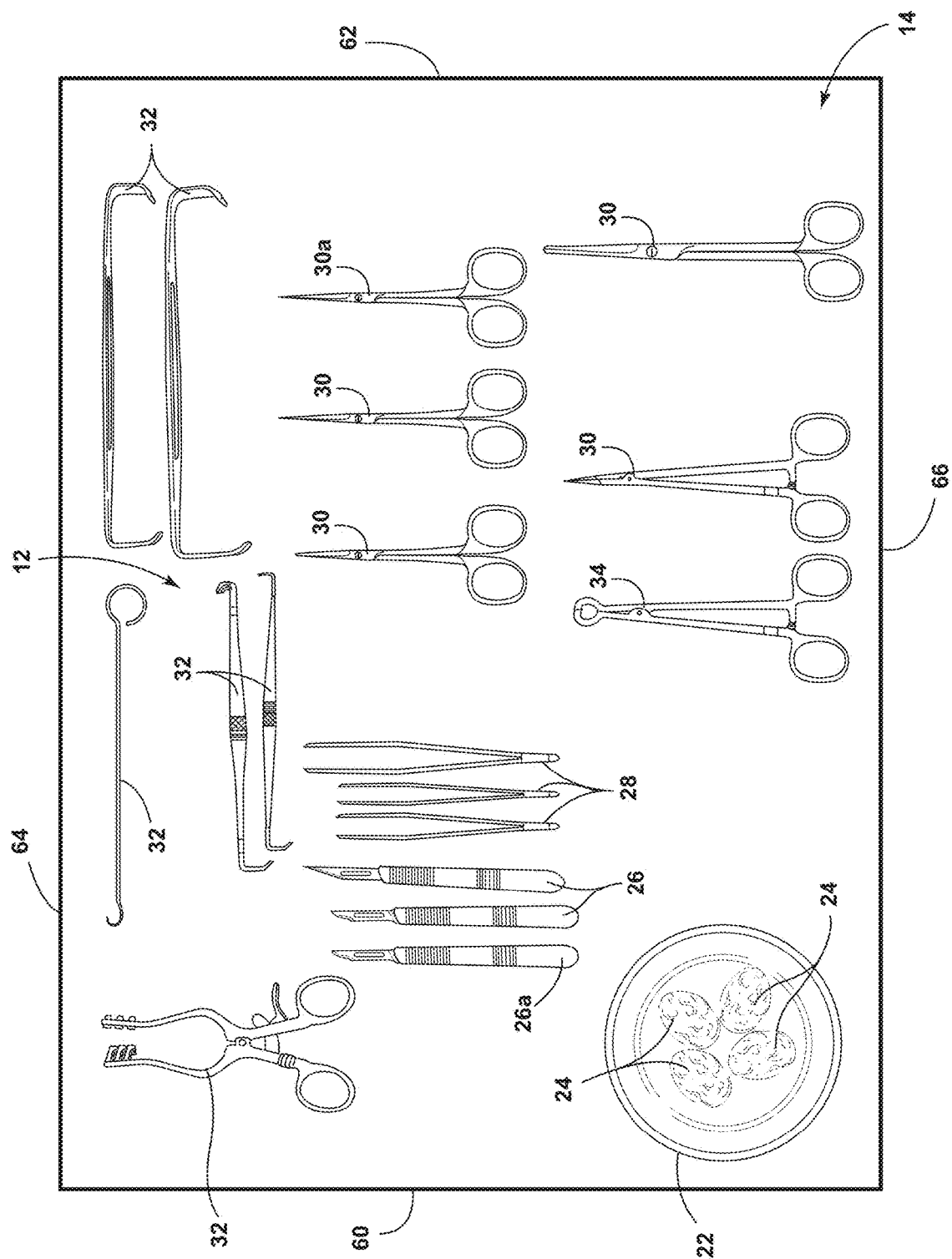
FIGS. 4A-4E illustrate top views of the surgical instruments on the surface of FIG. 2 after actual attributes of the surgical instruments have been changed to match desired attributes of the surgical instruments.
Figure 4B:
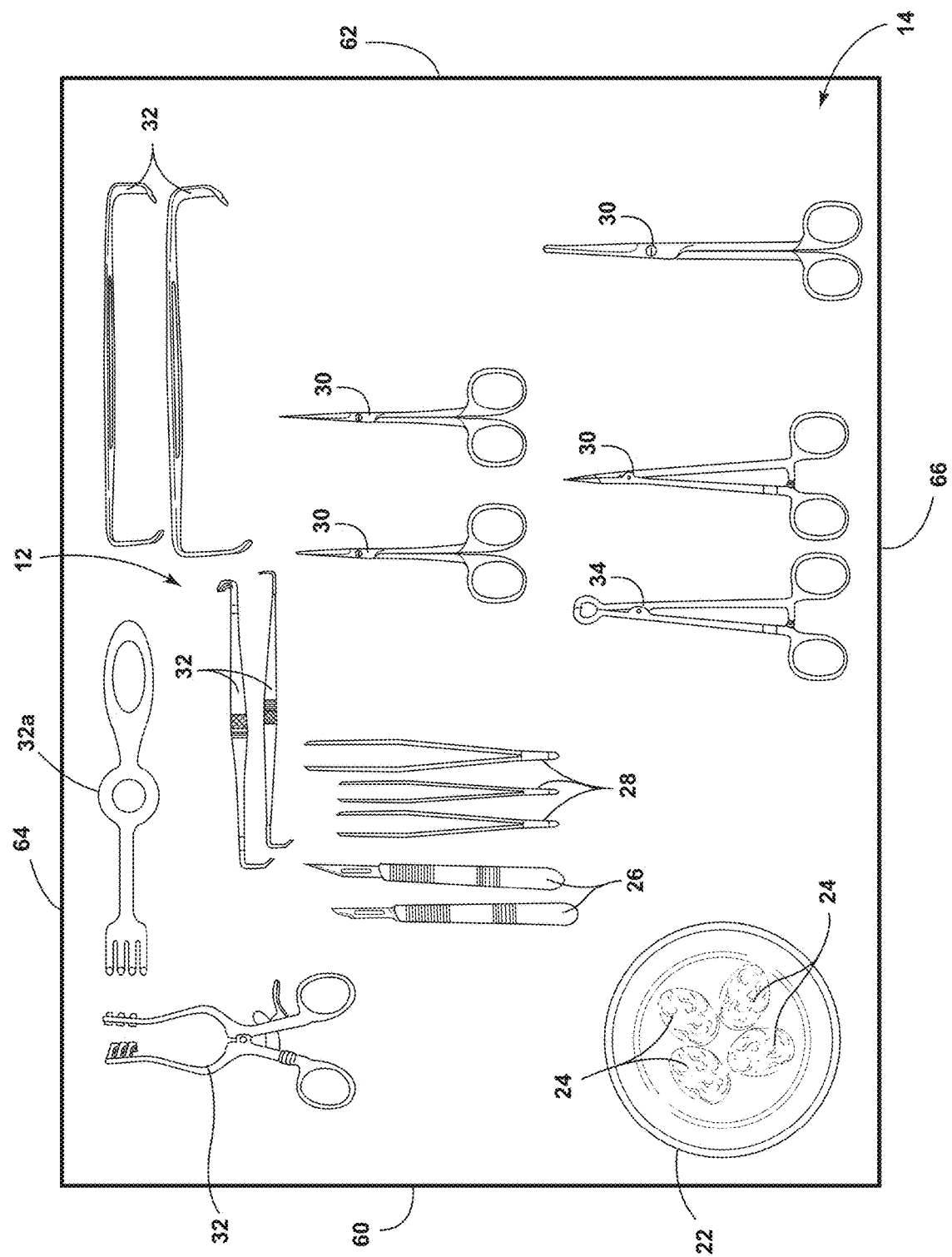
Figure 4C:
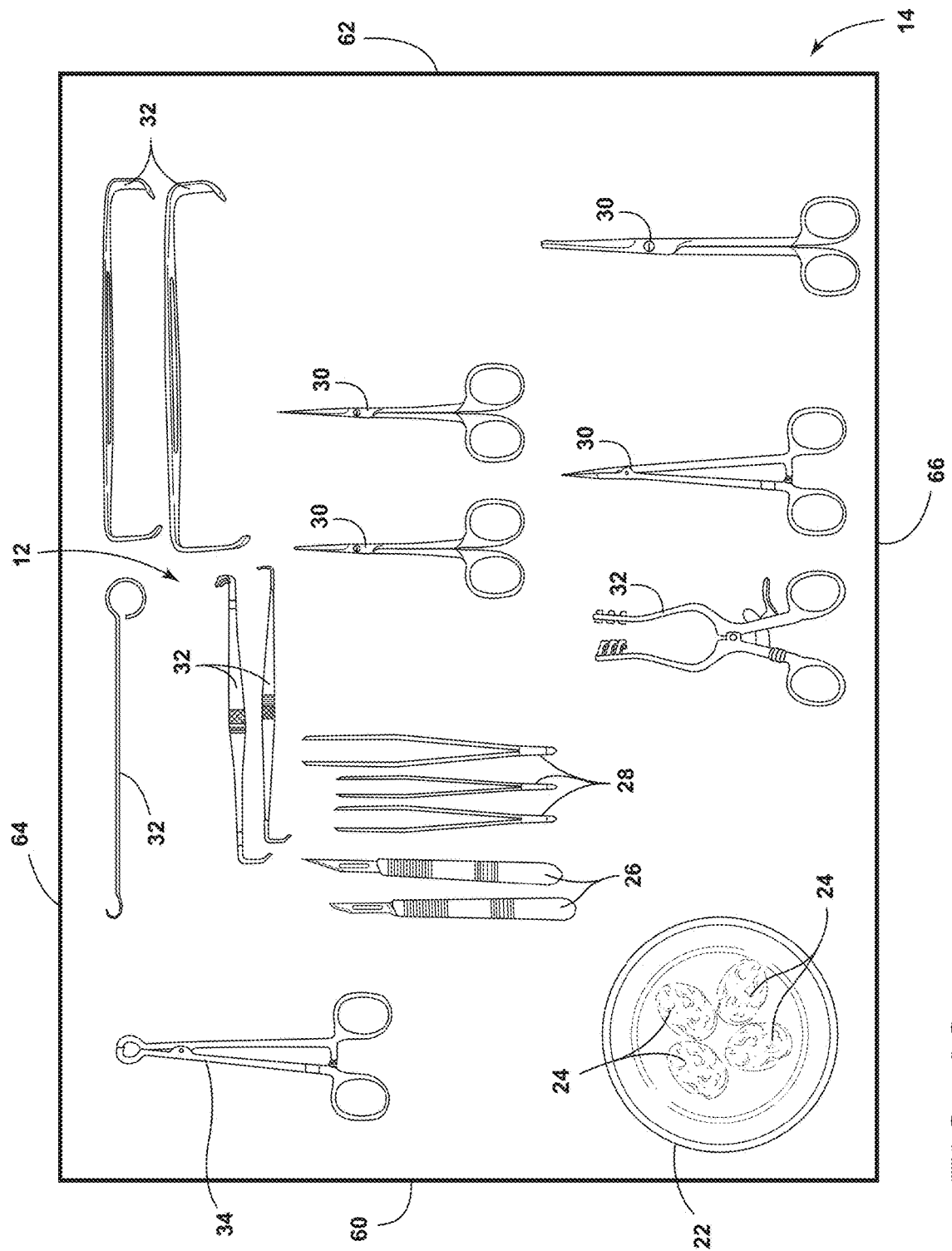
Figure 4D:
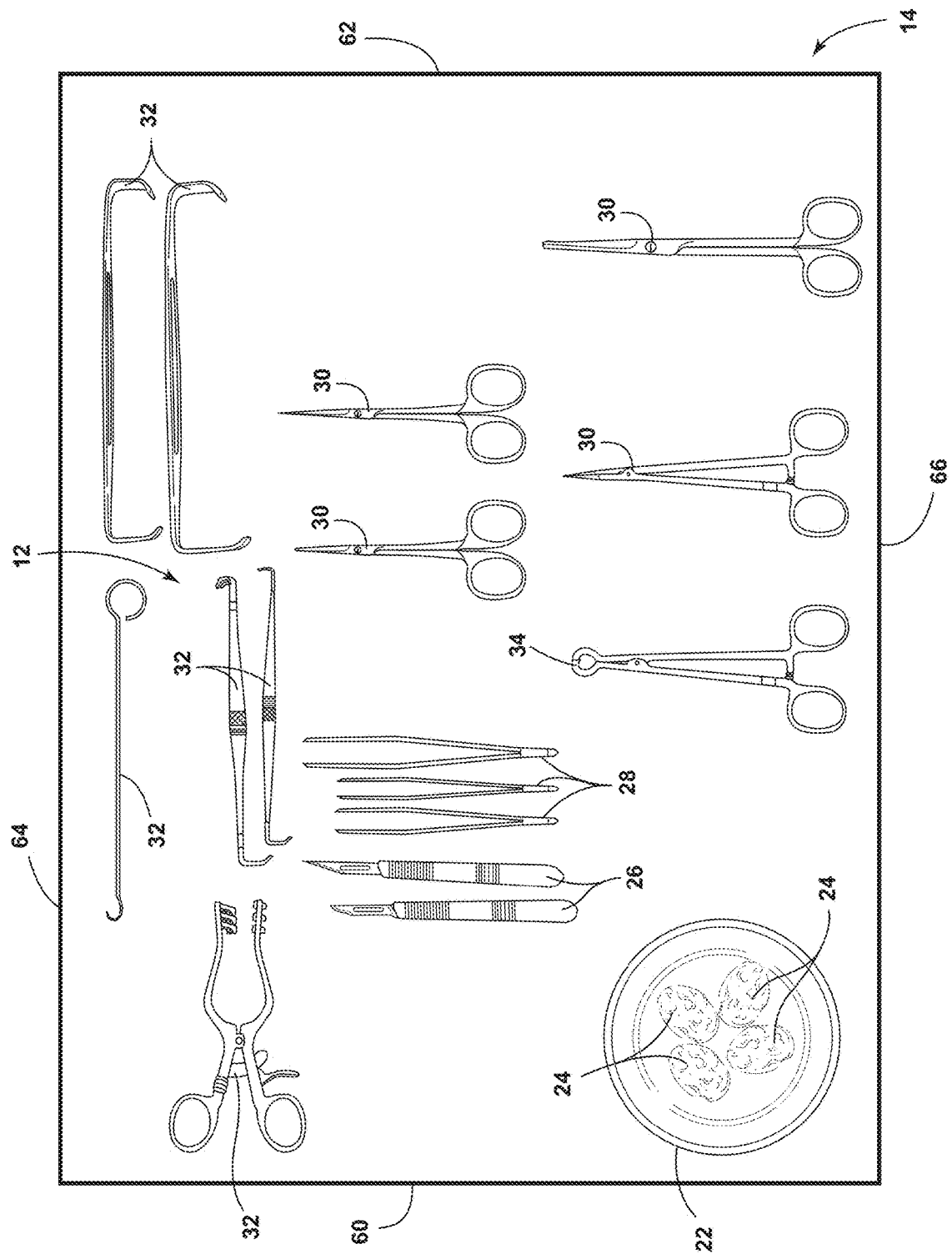
Figure 4E:
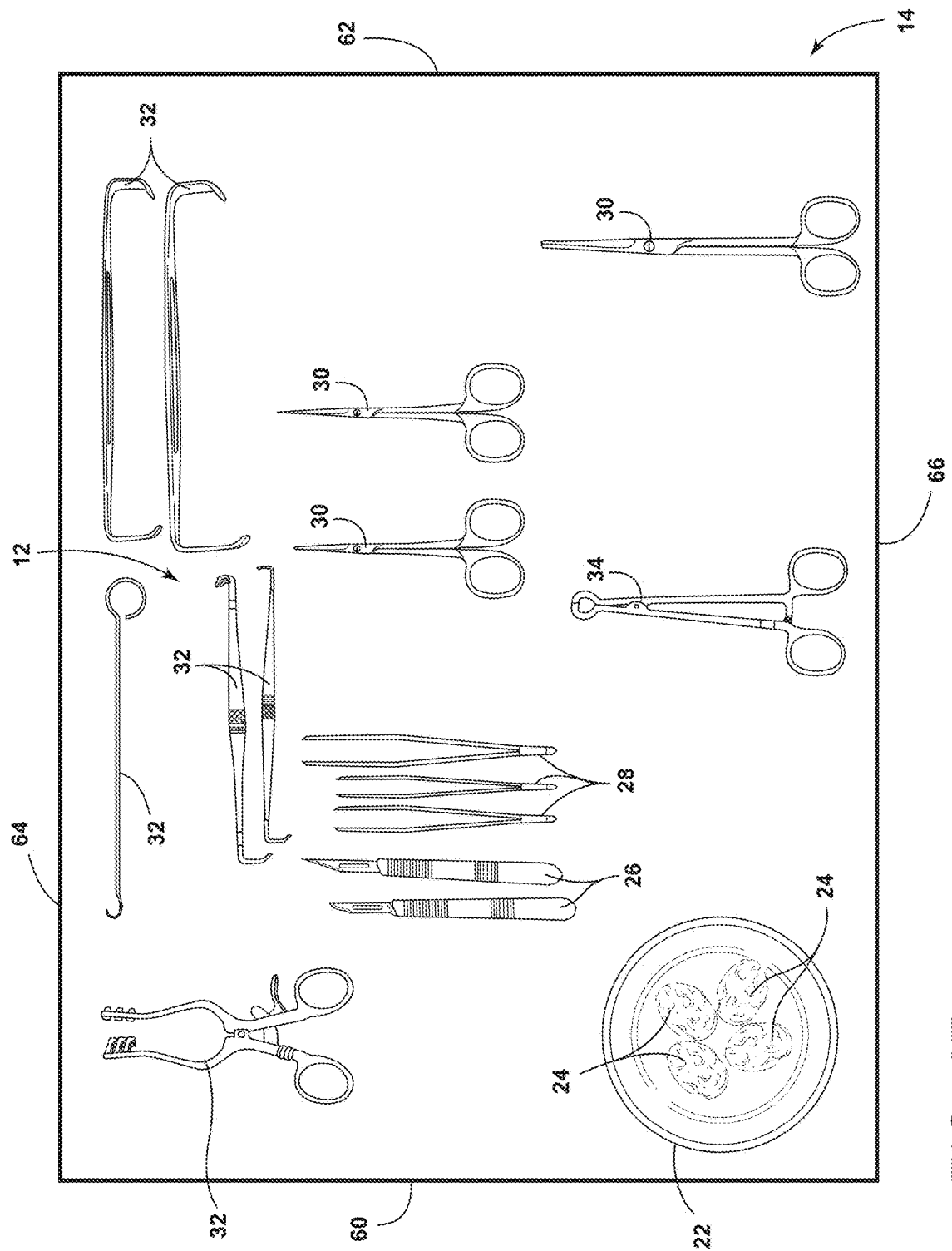

However, if the actual attributes of the surgical instruments 12 are not identical to the desired attributes as determined at decision step 72, the computer system 48 issues instruction information at step 76. The instruction information will provide instructions for correcting the actual attributes of the surgical instruments 12 to be identical to the desired attributes. The instruction information can include displaying the instruction information on a display or monitor 49 of the computer system 48 and/or providing audible directions over a speaker (not shown). The instruction information can include instructions for removing at least one of the surgical instruments 12, adding at least one surgical instrument 12 to the table 14 and/or moving locations of at least one of the surgical instruments 12. For example, the instruction information can include instructions to add another scalpel 26a and another scissors 30a as illustrated in FIG. 4A, substitute a Volkman retractor 32a for the Cushing decompression retractor 32 as illustrated in FIG. 4B, swap positions of the Weitlander retractor 32 and the sponge clamp 34 as illustrated in FIG. 4C, rotate the Weitlander retractor 32 by 90° as illustrated in FIG. 4D or remove one of the scissors 30 as illustrated in FIG. 4E.

In the illustrated example, after receiving the instruction information at step 76, the hospital personnel can then conform the actual attributes of the surgical instruments 12 to be identical to the desired attributes at step 78. It is contemplated that the method 40 of properly locating the surgical instruments 12 can return to step 44 after step 78 to ensure that the surgical instruments 12 are properly located.

A further aspect of the present invention is to provide the proper surgical equipment 16 in the proper location within the operating room 10. FIG. 1 illustrates surgical equipment 16 on the floor 18 or shelving 20 of the operating room 10. As illustrated in FIG. 1, examples of surgical equipment 16 include the image and video capture and recording device 50, a video camera 120 and an associated endoscope 138, the touchscreen monitor 49, a camera control unit 124, a scope light source unit 126, a printer 130, a fluid management pump 132, an insufflator 141, a shaver 136, an RF and shaver control 134 and an additional monitor 135. However, any piece of surgical equipment 16 that can be located within the operating room 10 can be used. The surgical equipment 16 can therefore include the overhead light 56 or another other item connected to a wall or a ceiling of the room (e.g., anything on a boom (for example, a monitor or boom shelving). Moreover, the surgical equipment 16 can be all of the surgical equipment 16 on a single portable cart 19a, 19b, 19c, 19d or the entire portable cart 19e itself. For example, the surgical equipment 16 can include an image capture cart 19a having the image and video capture and recording device 50, the video camera 120 and associated endoscope 138, the touchscreen monitor 49, the camera control unit 124, the scope light source unit 126 and the printer 130 thereon. Further examples of surgical equipment 16 include a pump cart 19b having the fluid management pump 132 thercon, a RF and shaver control cart 19c having the RF and shaver control 134 thercon, an insufflator cart 19d having the insufflator 141 thercon, a waste container cart 19c, an instrument cart 19f having the table 14 with the surgical instruments 12 thereon, and a patient surgical table 200. Further carts having any piece or pieces of surgical equipment 16 thereon can also be the surgical equipment.

One example of the surgical equipment 16 is the image and video capture and recording device 50 located in a control housing 121. The image and video capture and recording device 50 can output images and video on the touchscreen monitor 49, which can be integrated into the control housing 121. The image and video capture and recording device 50 can also output images and video to the additional monitor 135 via either a wired connection or wirelessly. The illustrated image and video capture and recording device 50 is therefore capable of displaying images and videos on the touchscreen monitor 49 and/or on the additional monitor 135 captured live by cameras and/or replayed from recorded images and videos.

The illustrated image and video capture and recording device 50 is also capable of recording images and videos. The image and video capture and recording device 50 can include an internal hard drive for storing captured images and videos and can also communicate with a picture archiving and communication system (PACS), as is well known to those skilled in the art, to save images and video in the PACS and for retrieving images and videos from the PACS. The image and video capture and recording device 50 can also display any saved images (e.g., from the internal hard drive or from the PACS) on the touchscreen monitor 49 and/or the additional monitor 135. It is contemplated that the image and video capture and recording device 50 could obtain or create images of a patient during a surgical procedure from a variety of sources (e.g., from video cameras, video cassette recorders, X-ray scanners (which convert X-ray films to digital files), digital X-ray acquisition apparatus, fluoroscopes, CT scanners, MRI scanners, ultrasound scanners, CCD devices, and other types of scanners (handheld or otherwise)).

Yet another example of the surgical equipment 16 is the camera control unit 124 that is coupled to the video camera 120 by a flexible electronic transmission line 140. The transmission line 140 conveys video data from the video camera 120 to the camera control unit 124 and also conveys various control signals bi-directionally between the video camera 120 and the camera control unit 124. The camera control unit 124 can be connected (wired or wirelessly) to the image and video capture and recording device 50 to provide the images and videos to the image and video capture and recording device 50. Video cameras 120 and camera control units 124 used with scopes 138 are well known to those skilled in the art. An example of the video camera 120 and camera control unit 124 for use with an endoscope is the 1488 HD Camera as sold by Stryker Corporation of Kalamazoo, MI.

Another example of the surgical equipment 16 is the light source unit 126 that transmits high intensity light into the patient through the scope 138 via a fiber optic cable 144. Light source units 126 used with scopes 138 are well known to those skilled in the art. An example of the light source unit 126 for use with the endoscope 138 is the L9000 LED Light Source as sold by Stryker Corporation of Kalamazoo, MI.

Yet another example of the surgical equipment 16 is the printer 130. The printer 130 can be connected to the image and video capture and recording device 50 for outputting images from the image and video capture and recording device 50. An example of the printer 130 is the SDP1000 Medical Grade Digital Printer as sold by Stryker Corporation of Kalamazoo, MI.

Another example of the surgical equipment 16 is the fluid management pump 132. The fluid management pump 132 is employed during surgical procedures to introduce sterile solution into surgical sites and to remove fluid and debris generated by the procedure. In the illustrated example, the fluid management pump 132 can supply the motive force for pumping the sterile solution through an inflow tube (not shown) into the surgical site via a cannula. The fluid management pump 132 can also supply the motive force for suctioning solution and any waste material removed from the surgical site from an outflow tube 147 to a waste tube 137 connected to the waste container cart 19c. In the illustrated example, the outflow tube 147 is connected to the shaver 136. An example of the fluid management pump is disclosed in U.S. Patent Application Publication No. 2013/0267779 entitled CONTROL FOR SURGICAL FLUID MANAGEMENT PUMP SYSTEM, the entire contents of which are hereby incorporated herein by reference. An example of the shaver 136 is the FORMULA® Shaver Hand Piece as sold by Stryker Corporation of Kalamazoo, MI.

Yet another example of the surgical equipment 16 is the RF and shaver control 134. The RF and shaver control 134 sends power to an ablation and coagulation device or electrosurgical tool (not shown) and/or the shaver 136. Ablation and coagulation devices are well known to those skilled in the art. An example of an ablation and coagulation device that can be connected to the RF and shaver control 134 is the SERFAS™ Energy Probe as sold by Stryker Corporation of Kalamazoo, MI. The RF and shaver control 134 sends power to the shaver 136 through a cable 143. An example of the RF and shaver control 134 is the CROSSFIRE® arthroscopic resection system as sold by Stryker Corporation of Kalamazoo, MI.

Another example of the surgical equipment 16 is the insufflator 141. The insufflator 141 is used to supply inert, nontoxic gases, such as carbon dioxide, into a body cavity, in order to expand the cavity, or to minimize visual obstruction during minimally invasive or laparoscopic surgery. An insufflator 141 is well known to those skilled in the art. An example of the insufflator 141 is the PNEUMOSURE® 45L Insufflator as sold by Stryker Corporation of Kalamazoo, MI. Further examples or surgical equipment 16 include stand alone pieces of surgical equipment 16 such as a portable monitor 135a and a portable overhead light 56a.

Figure 5:
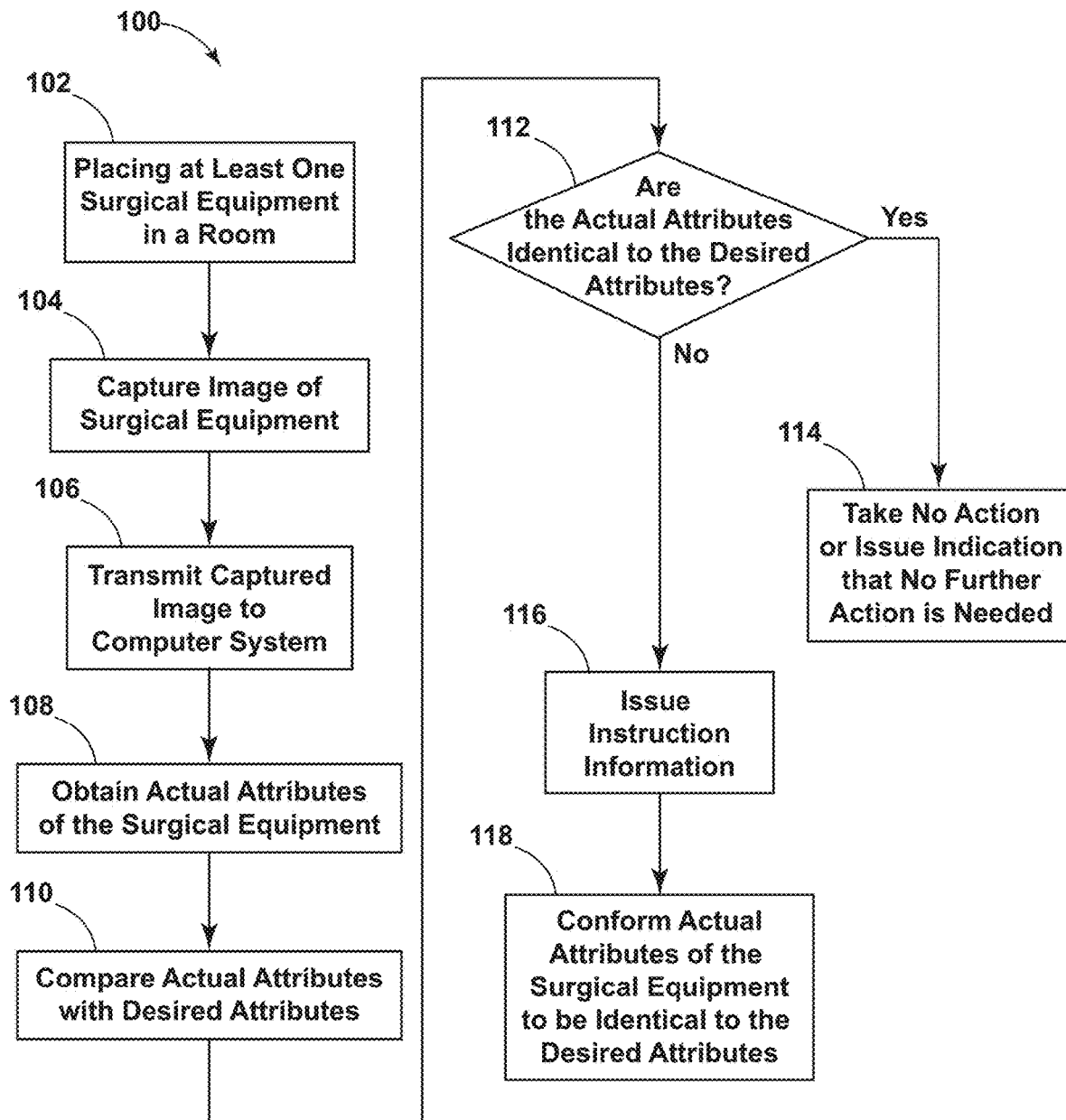
FIG. 5 illustrates a method of properly locating the surgical equipment in an operating room.

An aspect of the present invention is to ensure that the proper surgical equipment 16 is located in the operating room 10 and in the proper location in the operating room 10 according to preferences of particular medical personnel (e.g., a surgeon) or according to a particular procedure being performed. FIG. 5 illustrates a method 100 of properly locating the surgical equipment 16. In a first step of the method 100, at least one piece of surgical equipment 16 is placed or positioned in the operating room 10 at step 102. Typically, a plurality of pieces of surgical equipment 16 (stand alone, on carts or on shelving) are placed in the operating room 10 (sec, for example, FIG. 1) and positioned in a location in the room (e.g., a location of the surgical light 56 or any other fixed, but movable item in the room relative to the patient surgical table 200). After the surgical equipment 16 is placed and positioned in the operating room 10, a camera (e.g., the wall camera 36b as shown, a camera in the overhead light 56 or the camera of a tablet computer) captures an image of the surgical equipment 16 at step 104. The captured image of the surgical equipment 16 is then transmitted to the computer system 48 for analysis at step 106. The computer system 48 (e.g., desktop or laptop computer) can be located in the operating room 10 (or elsewhere) or can be the image and video capture and recording system 50. The camera 36 can transmit the image to the computer system 48 wirelessly or via a wired system.

After the computer system 48 receives the image of the surgical equipment 16 captured by the camera 36 at step 104, the computer system 48 obtains actual attributes of the surgical equipment 16 at step 108. The actual attributes of the surgical equipment 16 can include the number of each piece of surgical equipment 16, the style of the surgical equipment 16, the brand of the surgical equipment 16, the location/orientation of the surgical equipment 16 on the floor 18 or on a cart 19a, etc. and/or the presence of the surgical equipment 16 and/or a cart 19a, etc. with the surgical equipment 16 thereon. It is contemplated that other actual attributes of the surgical equipment 16 could be found. The actual attributes of the surgical equipment 16 can be found using an image recognition algorithm (e.g., using Haar Cascade classifier). Such image recognition algorithms are well known to those skilled in the art. It is also contemplated that the surgical equipment 16 could include a linear or matrix bar code thercon for determining the actual attributes of the surgical equipment 16. It is further contemplated that the surgical instruments 12 could include indicators thercon for assisting in determining the actual attributes of the surgical instruments 12. For example, two surgical instruments 12 may have the same outside configuration, but have different internal parts on components. In such a situation, the different surgical instruments 12 could include each include a different exterior visual indicator (e.g., a modulated infrared or other spectrum beacon, different colors, or different linear or matrix bar code thercon) to allow the computer system 48 to properly identify the surgical instrument 12.

For the example of the surgical equipment 16 on the floor 18 of the operating room 10 illustrated in FIG. 1, the actual attributes of the surgical equipment 16 could include the style of the surgical equipment 16. For example, the computer system 48 can determine the style of the shaver 136 (e.g., arthroscopic shaver or ENT shaver) and/or the brand (i.e., manufacturer) of the shaver 136. The actual attributes of the surgical equipment 16 could also include the location of the surgical equipment 16 in the operating room 10 or in relation to the surgical table 200 configured to support a patient thereon during surgery, the location of the surgical table 200 in the room, the height and orientation of the surgical table 200, or the location of the surgical equipment 16 on a particular shelf on a particular one of the carts 19a, etc. For example, the computer system 48 can determine the location (including orientation) of the surgical equipment 16 on the carts 19a, etc. or the location of the carts 19a. Moreover, actual attributes of the surgical instruments 12 could further be a determination of the presence of the surgical equipment 16. For example, the computer system 48 can determine that the carts 19a-19e are in the operating room 10. The actual attributes can be a combination of any of the above-noted actual attributes.

After the computer system 48 obtains actual attributes of the surgical equipment 16 at step 108, the computer system 48 compares the actual attributes of the surgical equipment 16 with desired attributes of the surgical equipment 16 at step 110. The desired attributes of the surgical equipment 16 are stored in a digital preference storage. The digital preference storage can be saved in the computer system 48 or retrievable by the computer system 48 as outlined above.

In the method 100 of properly locating the surgical equipment 16, if the actual attributes of the surgical equipment 16 are identical to the desired attributes as determined at decision step 112, no further action is taken or the computer system 48 issues instruction information indicating that no further action is needed at step 114. The computer system 48 can issue an indication that no further action is needed using any visual and/or audio notification. For example, the computer system 48 can issue an "OK" message on the display or monitor 49, can flash a green light, can issue audio stating that all of the surgical equipment 16 are proper and in the correct location or any combination of the above.

However, if the actual attributes of the surgical equipment 16 are not identical to the desired attributes as determined at decision step 112, the computer system 48 issues instruction information at step 116. The instruction information will provide instructions for correcting the actual attributes of the surgical equipment 16 to be identical to the desired attributes. The instruction information can include displaying the instruction information on a display or monitor 49 of the computer system 48 and/or providing audible directions over a speaker (not shown). The instruction information could also include instructions for locations of pieces of surgical equipment 16 that is not in the room 10 but should be in the room 10. The instruction information can include instructions for removing at least one of the pieces of surgical equipment 16 (including carts 19a, etc.), adding at least one piece of surgical equipment 16 (including carts 19a, etc.) to the room 10 and/or moving locations of at least one of the pieces of surgical equipment 16 (including carts 19a, etc.).

Figure 6A:
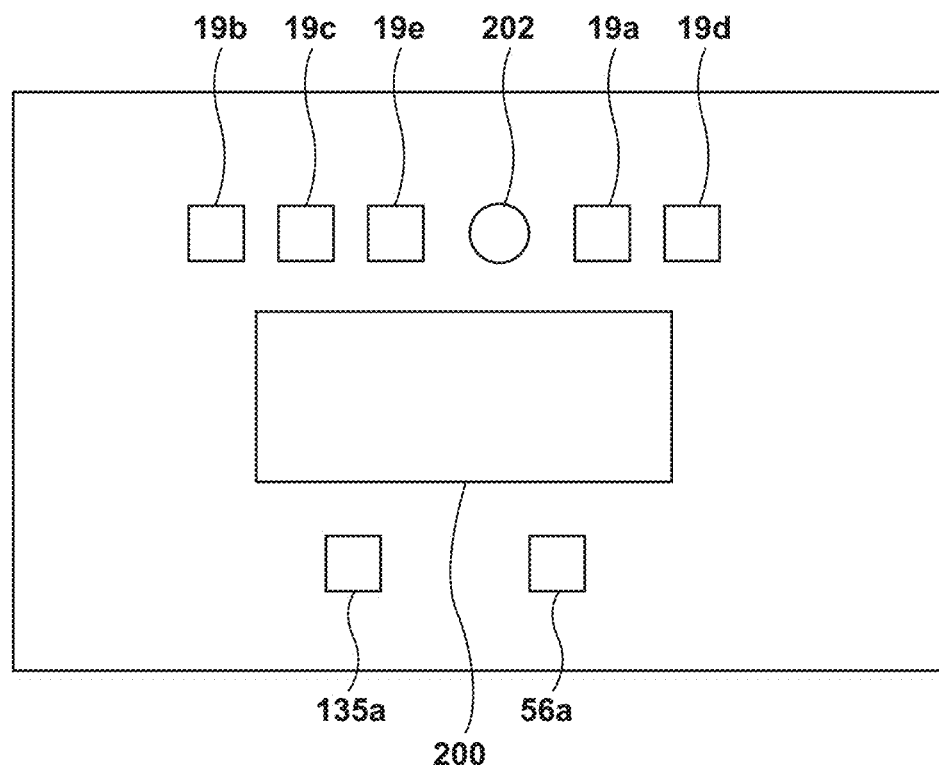
FIGS. 6A-6E illustrate schematic top views of the operating room of FIG. 1 before (FIG. 6A) and after (FIGS. 6B-6E) actual attributes of the surgical equipment have been changed to match desired attributes of the surgical equipment.
Figure 6B:
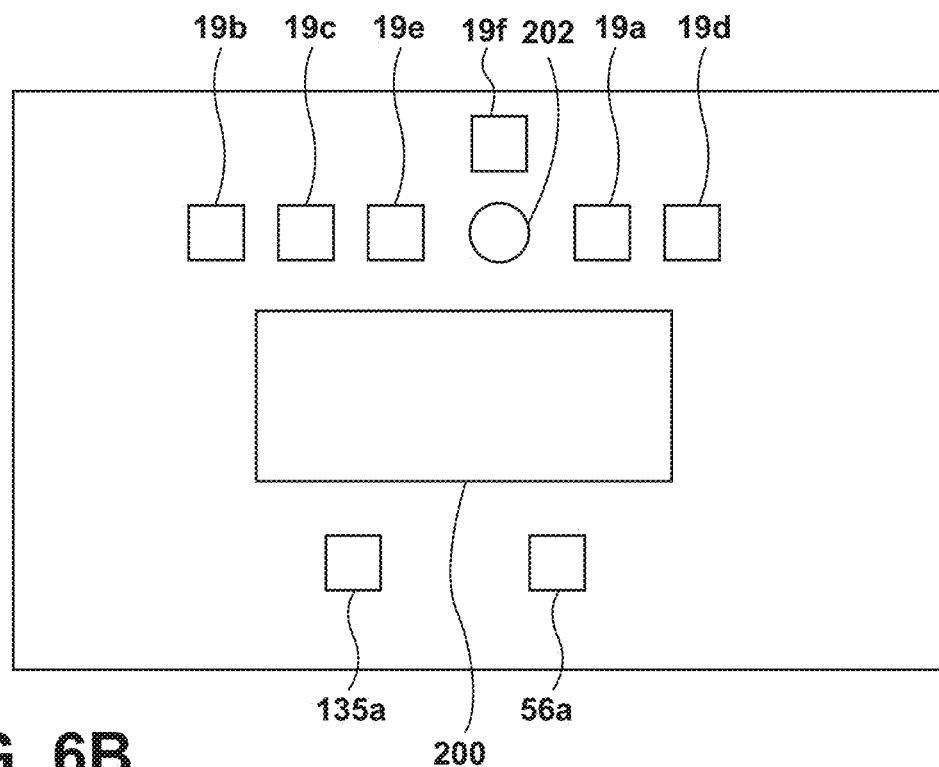
Figure 6C:
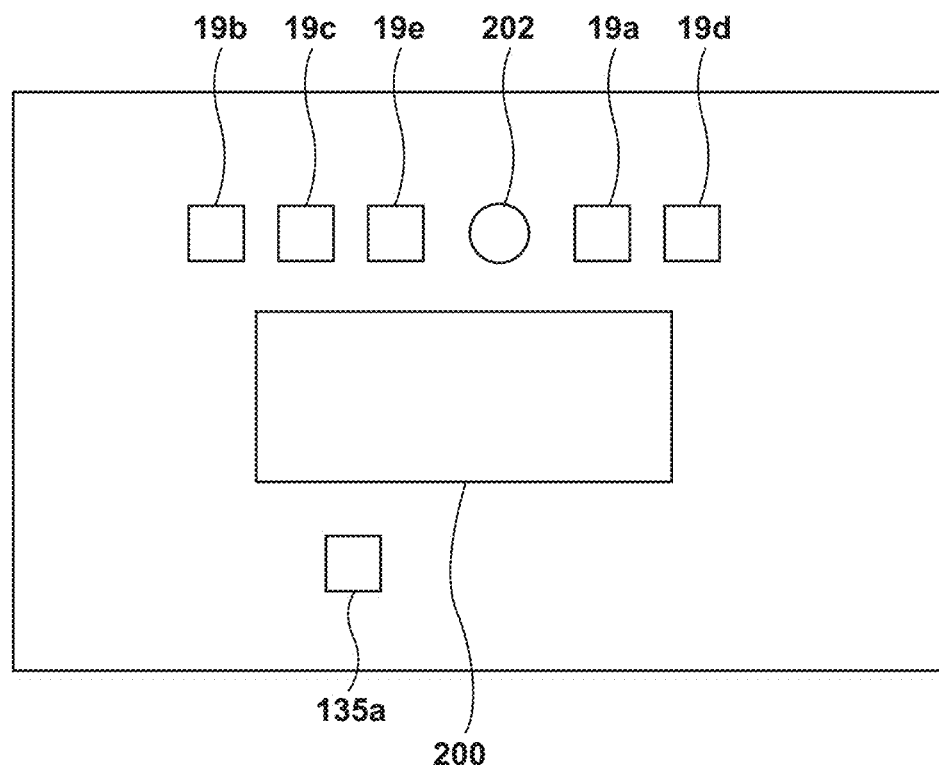
Figure 6D:
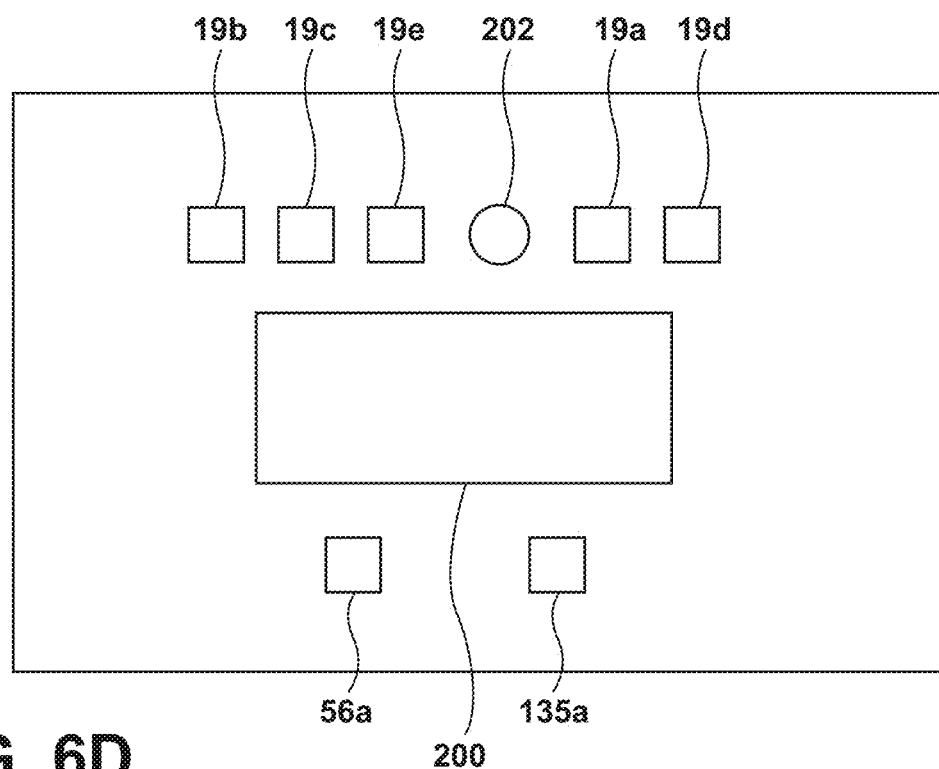
Figure 6E:
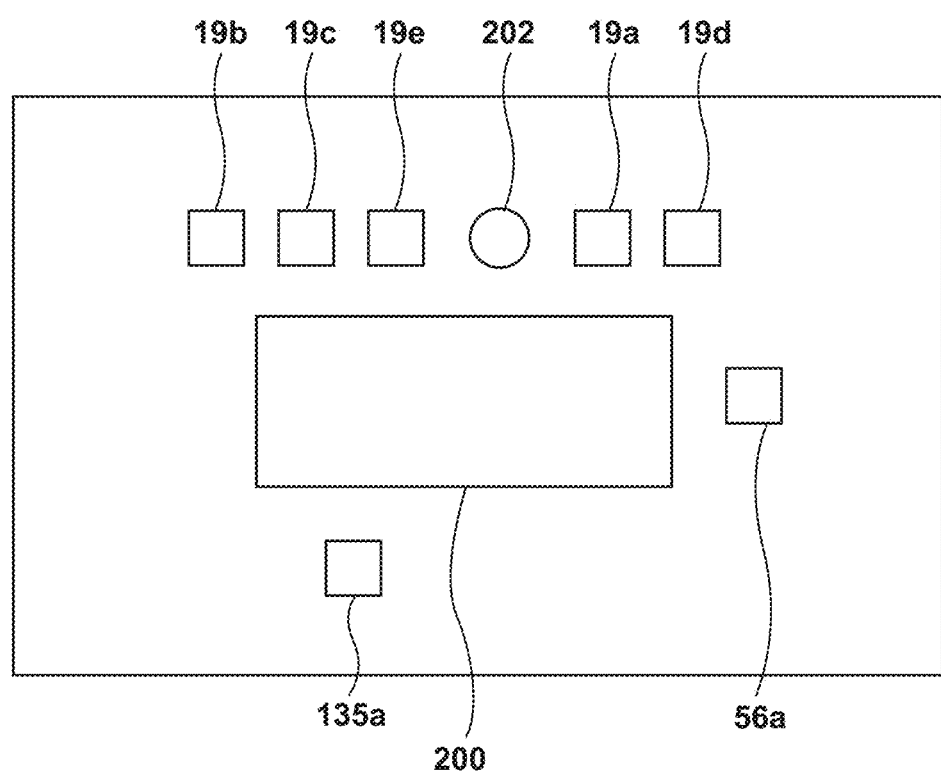

For example, the instruction information can include instructions to add surgical equipment, remove surgical equipment or rearrange the surgical equipment 16 in the operating room 10. FIG. 6A illustrates an initial arrangement of an operating room 10 with the image capture cart 19a, the pump cart 19b, the RF and shaver control cart 19c, the insufflator cart 19d, and the waste container cart 19e on a first side of the table 200 and with a space 202 for the surgeon with the image capture cart 19a and the insufflator cart 19d on a first side of the space 202 and the pump cart 19b, the RF and shaver control cart 19c and the waste container cart 19e on a second side of the space 202. FIG. 6A also includes the portable monitor 135a and the portable overhead light 56a on a second side of the table 200. The instruction information can include instructions to add an instrument cart 19f having the table 14 with the surgical instruments 12 thereon adjacent the space 202 for the surgeon as illustrated in FIG. 6B, remove the portable overhead light 56a as illustrated in FIG. 6C, swap positions of the portable overhead light 56a and the portable monitor 135a as illustrated in FIG. 6D, or move the portable overhead light 56a to an end of the table 200 as illustrated in FIG. 6E. The examples of FIGS. 6A-6E are for illustrative purposes only and are not exhaustive examples of the rearrangements that can be made according to the instruction information. It is contemplated that the instruction information can also include instructions for moving surgical equipment 16 between different shelves on a single cart 19a, etc. or to change some of the surgical equipment 16 on a single cart 19a, etc.

In the illustrated example, after receiving the instruction information, the hospital personnel can then conform the actual attributes of the surgical equipment 16 to be identical to the desired attributes at step 118. It is contemplated that the method 100 of properly locating the surgical equipment 16 can return to step 104 after step 118 to ensure that the surgical equipment 16 is properly located.

It is contemplated that the computer system 48 can be programmed to observe the layout of the surgical devices in the operating room 10 and record the actual attributes of the surgical devices to form the desired attributes of the surgical devices to be stored in the digital preference storage. It is further contemplated that the computer system can obtain desired configurations for the surgical equipment from the digital preference storage associated with a particular person to be using the operating room (e.g., surgeon) and/or with a particular procedure to be performed and configure the surgical equipment according to the desired configurations. For example, the procedure for configuring surgical equipment as set forth in U.S. Patent Application No. 62/100,286 entitled METHOD OF CONFIGURING DEVICES IN AN OPERATING THEATER, the entire contents of which are hereby incorporated by reference, can be used.

Another aspect of the present invention is to obtain images of numerous people/personnel 400 and objects in a medical facility and saving and analyzing the images to improve efficiency of the medical facility. In this aspect of the present invention, sensors and/or cameras 320 are located throughout the medical facility to track potentially everything moving within the medical facility.

Figure 7:
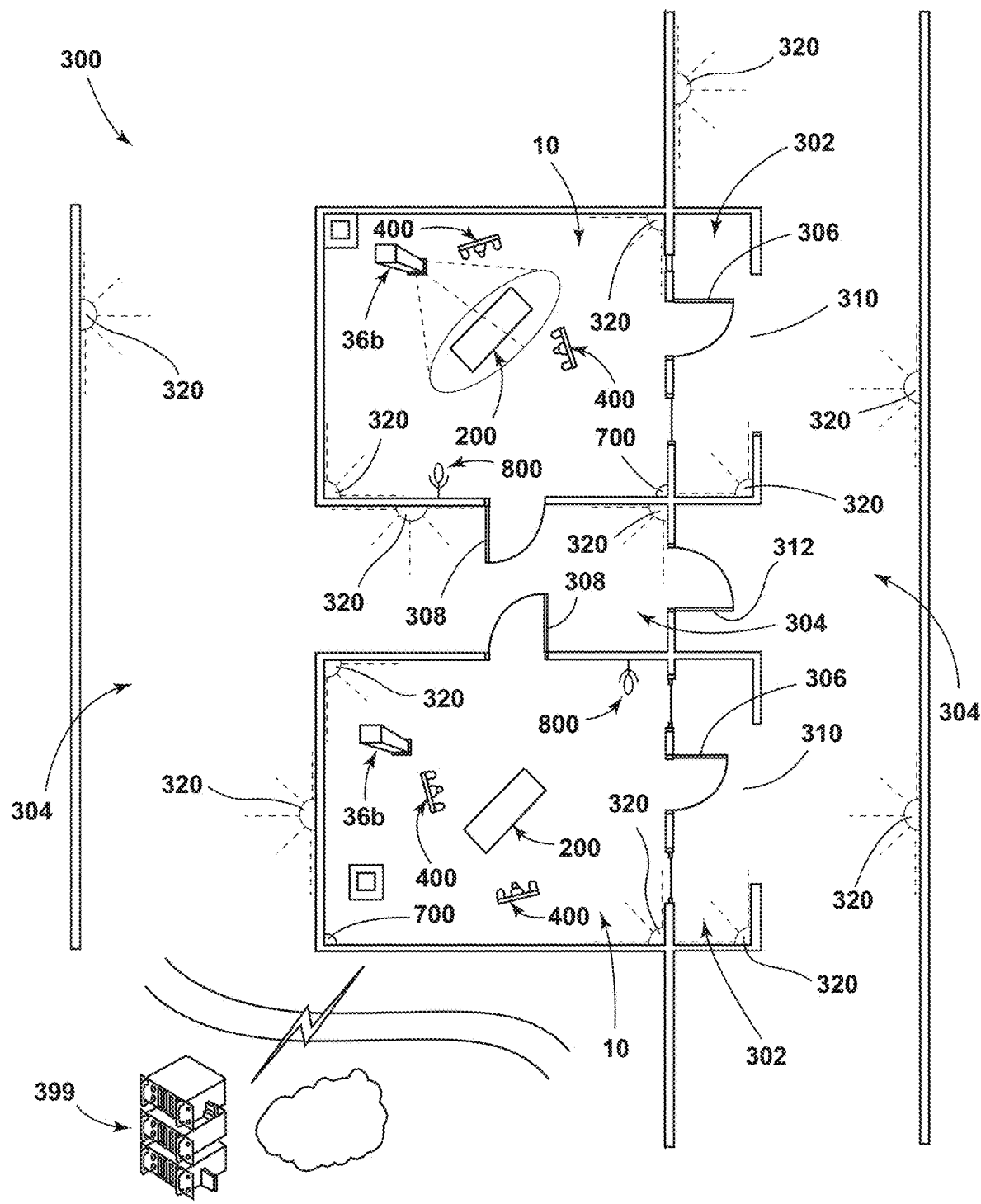
FIG. 7 illustrates a schematic view of a floor of a medical facility.

FIG. 7 illustrates a schematic view of a floor 300 of a medical facility. The illustrated floor 300 includes a plurality of the medical care areas 10, entrance areas 302 for the medical care areas 10, and hallways 304. Care area doors 306 allow entrance from the entrance areas 302 to the medical care areas 10, medical entrance doors 308 allow entrance from the hallways 304 to the medical care areas 10, entrance openings 310 allow entrance from the hallways 304 to the entrance areas 302, and hallway doors 312 are located between different sections of hallways 304. In FIG. 7, the camera and/or sensors 320 are located in the hallways 304, in the entrance areas 302 and the medical care areas 10 to allow for viewing everywhere in the medical facility and particularly at the care area doors 306, the medical entrance doors 308, the entrance openings 310 and the hallway doors 312 to view ingress and egress of people/personnel 400 and devices through those areas. While the camera and/or sensors 320 are illustrated as only being in the hallways 304, in the entrance areas 302 and in the medical care areas 10, it is contemplated that the camera and/or sensors 320 could be located throughout the medical facility. For example, the camera and/or sensors 320 could be located at entrances to the medical facility, at elevators doors, at stair doors, at patient rooms, in storage rooms, in waiting rooms, in operating rooms, at an emergency department, in a catheterization lab, throughout a labor and delivery floor, at a preoperational unit, at a post anesthesia care unit, at intensive care units, at radiology, at a hospital pharmacy, at a facilities management area and at a sterile processing department. The above list is for example purposes only and is not exhaustive.

The illustrated camera and/or sensors 320 can potentially track everything moving through the viewing area of the camera and/or sensors 320. The camera and/or sensors 320 may be active or passive and can capture images or sense personnel, movement and medical devices (and other objects). The camera and/or sensors 320 can have a wide-angle lens and processing software that tracks personnel, movement, medical devices (and other objects) and patterns. The camera and/or sensors 320 can also have the capability to capture depth information using an active scanning method (e.g., a 3D scanner as is well known in the art). The camera and/or sensors 320 can capture images in color, black and white, or in the infrared. Examples of the camera and/or sensors 320 can include the room camera 36b fixed to walls 52 or the ceiling 54 of the room 10 as outlined above and the camera 36c in the overhead light 56. It is contemplated that the camera and/or sensors 320 can include a combination of motion sensor and camera wherein the camera is activated when motion is sensed by the motion sensor. It is further contemplated that the camera and/or sensors 320 can be composed of sensors that can sense passage of personnel and medical devices without capturing an optical image thereof (e.g., by reading RFID chips on the personnel and medical devices).

In the illustrated example, the captured images and/or sensed personnel and medical devices (and other items) are processed to determine the personnel and medical devices (and other items) passing through an area in front of the camera and/or sensors 320. It is contemplated that the camera and/or sensors 320 can have an on-board computer system to analyze the personnel and medical devices (and other items) to determine the characteristics thereof. For example, the camera and/or sensors 320 can have a computer system that includes one or more processors or other similar control devices as well as one or more memory devices. The processor controls the overall operation of the computer system and can include hardwired circuitry, programmable circuitry that executes software, or a combination thereof. The processor may, for example, execute software stored in the memory device. The processor may include, for example, one or more general- or special-purpose programmable microprocessors and/or microcontrollers, application specific integrated circuits (ASICs), programmable logic devices (PLDs), programmable gate arrays (PGAs), or the like. The memory device may include any combination of one or more random access memories (RAMs), read-only memories (ROMs) (which may be programmable), flash memory, and/or other similar storage devices. It is contemplated that the computer system for the camera and/or sensors 320 can run an image recognition algorithm (e.g., using Haar Cascade classifier) to analyze the personnel and medical devices (and other items) to determine the characteristics thereof. It is further contemplated that the personnel and medical devices (and other items) could include indicators thereon (e.g., different exterior visual indicators as outlined above) for assisting in determining the characteristics thereof. For determining the identity of the personnel, facial recognition and/or other features (e.g., height, walking gait, clothing, etc.) can be employed to properly identify the particular personnel. The computer system for the camera and/or sensors 320 can then send the aggregate information on the personnel and medical devices (and other items) to a central computer system 399 (via a wired system or wirelessly). Alternatively, the camera and/or sensors 320 can send captured images and/or sensed information to the central computer system 399 (via a wired system or wirelessly) for recognition and analysis by the central computer system 399. The central computer system 399 can also include one or more processors or other similar control devices as well as one or more memory devices as outlined above.

The illustrated central computer system 399 uses the information on the personnel and medical devices (and other items) along with further information to identify and measure opportunities for efficiency improvements that exist with a day of surgery workflow, optimize room design elements by specifying equipment placement and personnel movement, and standardize care in an effort to improve patient outcomes. One example of further information is usage details of medical devices 16. For example, the amount of usage of the shaver 136 (e.g, speed and time), type of images recorded in the image and video capture and recording device 50, type of light emitted from the scope light source unit 126, type and/or amount of fluid passed using the fluid management pump 132, usage of the insufflator 141, and usage of an additional monitor 135, with all of this information being sent to the central computer system 399 (either directly or through another system (e.g., from the image and video capture and recording device 50 when the image and video capture and recording device 50 is connected to the other medical devices 16 in the room 10)). The above list is for example purposes only and is not exhaustive. The usage details from the medical devices 16 can be retrieved by the central computer system 399 or can be sent to the central computer system 399 at a rate dependent and unique to each medical device 16. Moreover, the method 100 of properly locating the surgical equipment 16 can include an associated method of properly locating personnel 400. In the associated method of properly locating personnel 400, facial recognition software can be used to determine the personnel 400 in the room 10 and providing instruction information in the method 100 could also include instructions for adding essential personnel for a particular procedure that are currently absent from the room 10. For determining the identity of the personnel, other features in place of or in addition to facial recognition (e.g., height, walking gait, clothing, etc.) can be employed to properly identify the particular personnel.

Figure 8:
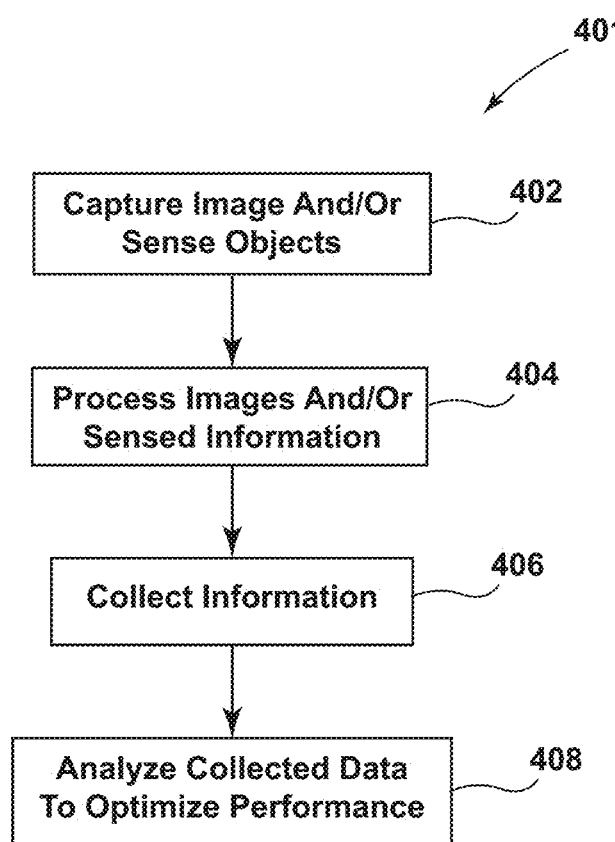
FIG. 8 illustrates a method of improving efficiency in the medical care facility according to an aspect of the present invention.

FIG. 8 illustrates a method 401 of improving efficiency in the medical facility. In a first step of the method 401, images of personnel and/or medical devices (and other items) are captured or the personnel and/or medical devices (and other items) are sensed using the cameras and/or sensors 320 at step 402. The images and/or the sensed information is then processed at step 404 to determine the characteristics of the personnel and/or medical devices (and other items) (e.g., identity of the personnel). Further information is then collected at step 406, with all of the information, images and other sensed items comprising collected data. The central computer system 399 is capable of residing on or being connected to the existing network of the medical facility to obtain the further information. The further information can be obtained for the hospital information system ("HIS"), the electronic medical record ("EMR") and/or scheduling system (which keeps track of patients and the reason and timing for their visit (e.g., location, time and type of surgery)). The further information will enable the system to aggregate case-specific information including: staff assigned to a given case, procedure type, original scheduled time, actual start time, and other data pertinent to analyzing workflow and efficiency. It is contemplated that the central computer system 399 can be capable of operating on a standalone isolated system separate from the hospital IT network, HIS, EMR, and scheduling system such that the further information would not include information obtainable from these networked databases.

Finally, the collected data is analyzed at step 408 to optimize the performance to thereby improve efficiency in the medical facility. The analyzed data can be used to identify and measure opportunities for efficiency improvements that exist. Software data processing can provide actionable intelligence in real-time or on-demand to predefined user groups. The software data processing can be done locally on-site on custom processing hardware or on available server infrastructure, or done remotely in a cloud configuration. The computer system can provide reports and alerts to nurses, surgeons, technicians, and administrators. The collected data can be stored, analyzed, and available per surgeon/procedure, patient, and institution, and can be used to assist the surgical staff in standardizing care across surgical units, institutions, and regions.

One example of an opportunity for improving efficiency is by tracking personnel movement and patterns. The tracking information can include tracking patient, physician, scrub tech, nurse/non-scrub, personnel not assigned to a current procedure, and unidentified non-hospital personnel entry into and exit from the room 10. Facial recognition software can be employed in step 404 of the method 401 to determine the identity of the personnel. Other features in place of or in addition to facial recognition (e.g., height, walking gait, clothing, etc.) can be employed to properly identify the particular personnel. Such personnel information can be analyzed (along with further information) to determine, for example, the most efficient personnel for a procedure, for tracking the personnel to improving staffing policies and for determining if improved security is needed.

In the illustrated example, the facial recognition and/or other features as outlined above can be used to determine the personnel 400 in the room 10 and saved as part of the medical record. It is contemplated that the cameras 320 including room camera 36b fixed to walls 52 or the ceiling 54 of the room 10 (e.g., the room camera 36b as shown or a camera 36c in an overhead light 56), a 360° camera, a wide-angle camera, a camera on the computer system 48, the video camera 120 and/or any other camera in the room 10 can be used in the process of identifying the personnel 400 in the room 10. Once the images of the personnel 400 in the room 10 are obtained, facial recognition and/or other features as outlined above can be used to determine the identity of the personnel 400. It is contemplated that the cameras 320 can take an image of everyone in the room 10 at a particular time (e.g., automatically (for example, when the room is scheduled to have surgery performed therein) or manually (for example, by pressing an icon on a touchscreen attached to the computer system 48)). It is also contemplated that the cameras 320 can take images of the personnel 400 in the room 10 over a series of time frames or constantly (e.g., every minute during the time the procedure is scheduled, every time one of the doors 306, 308 is opened or constant viewing looking for any additional personnel 400 that enters the room 10). The opening of the doors 306, 308 can be viewed using cameras and/or determined from barometric changes in the room. Once the identity of the personnel 400 in the room 10 is determined, a record of the personnel 400 can be saved automatically or manually to the record of the patient (e.g., in the EMR). The identity of the personnel 400 in the room 10 can also be saved in an operative note of the procedure. For example, the personnel 400 in the room 10 during a procedure can be saved in a surgical note created using the process set forth in U.S. patent application Ser. No. 14/853,289 entitled INTRA-SURGICAL DOCUMENTATION SYSTEM.

In the illustrated example, it is contemplated that the facial recognition and/or other recognition techniques as outlined above can be used to confirm the identity of the personnel 400 after the identity of the personnel 400 has been entered into the computer system (e.g., automatically from a scheduling program or manually) or after the identity of the personnel 400 has been identified using another automatic system (e.g., by reading an RFID chip worn by the personnel). Mismatches between the reading using facial recognition and/or other recognition techniques as outlined above and the identity of the personnel 400 entered into the computer system or identified using another automatic system can be flagged for additional review. If the personnel 400 is not entered into the computer system or identified using another automatic system, the identity of the personnel 400 can be confirmed in other manners (e.g., having the personnel 400 speak their name for recordation or enter their name into the computer system). It is further contemplated that the computer system can raise an alarm if improper or blacklisted personnel 400 are in the room.

Another example of an opportunity for improving efficiency is by tracking setup and cleanup of the room 10. For example, the following can be tracked: number of personnel involved, total time of setup and/or cleanup, active working time vs. idle time, time between completion of cleanup and start of next case setup, and time for setting up the room 10 per procedure type. The cameras and/or sensors 320 can capture images and/or sense information in the room 10 (in step 402) and the further information (e.g., schedule for the room and timing) (in step 406) can be analyzed in step 408 to improve the efficiency of cleaning up and setting up the room 10. For example, the quickest clean ups and set ups can be analyzed to determine the most efficient method of cleaning up and setting up the room 10 to be used in future clean ups and set ups. Moreover, personnel can be rerouted to other areas during their idle time to improve the efficiency of the personnel. Furthermore, the time between clean up and start of next setup can be analyzed to reduce the time the room 10 is not being used to maximize use of the room 10.

The analyzed data can also be used for optimizing room design elements for the room 10 and other areas accessed during the day of surgery. The impacted design elements include (but are not limited to): floor plan layout, reflective ceiling plan, equipment placement, optimal staff positioning, storage requirements, optimal size of treatment area, and general workflow efficiency improvements within the hospital. The collected information can include a height of the patient surgical table 200, position of surgical scrubbed staff and physician per procedure, movement of non-scrubbed personnel, entry/exit path of patient, entry/exit path of intra-operative equipment, recognition of case preferences (e.g., where equipment, instruments, and other supplies are placed/positioned per procedure type), movement/positioning of ceiling mounted equipment, number of times equipment was moved or reconfigured, equipment usage/durations. The efficiency of the room can be optimized by analyzing the collected information and specifying equipment placement and personnel movement in future procedures.

The analyzed data can further be used for optimizing infection control and sterile processing. For example, the number of infection incidents, location of infection incidents, number of personnel entries into and exits from the room 10 through the doors 306, 308, duration that the doors 306, 308 are open, number of sterile field violations (i.e., non-scrubbed personnel within 12 inches of the sterile field or sterile back table), sterile field transfer protocol violations, sterile processing department staff time spent on cleaning of the instruments 12, sterile processing department workflow process, and a percentage of critical areas cleaned (e.g., by visually determining whether an area was wiped/cleaned). Such information can be analyzed to reduce infections or to see where infections occur to determine which actions can be taken in the future to reduce the possibility of infection. For example, it is contemplated that the number of times the doors 306, 308 are opened can be associated with post-operative infection information to determine if there is a correlation between the number of times the doors 306, 308 are opened and post-operative infection. If there is a correlation, the medical center can establish procedures for an allowable number of door openings during a particular procedure. Such information (e.g., number of door openings) could be saved with the patient record (e.g., in the EMR). The system could also ascertain a reason for the doors to be opened and a reason for the ingress/egress of personnel for improving workflow efficiency and planning. For example, if a particular type of nurse or doctor has to leave the room 10 several times or enter/exit after the beginning of a procedure, such information could be used to assist in better allocating the schedule and time of that person. Furthermore, the idle time of particular personnel (or type of personnel (e.g., nurse)) could be determined to allow for the particular personnel (or type of personnel (e.g., nurse)) to be reallocated during the typical idle times thereof.

The analyzed data can also be used for optimizing care of a patient. For example, the following information can be tracked: active vs. idle time of each staff member during a procedure, drug administration times and medication error, improvements of the patient over time, delay in treatment, patient movement/lack of movement, patient fall warning/traceability, and location of surgery. If the central computer system 399 determines that something is improper after analyzing the data, the central computer system 399 can provide warnings (e.g., warning of potential wrong-site surgery) to improve care of the patient.

The analyzed data can further be used for attempting to determine causes for readmission of a patient. For example, the following information can be obtained: op/post-op traceability, a patient readmission to metrics that occurred during their continuum of care (admission to discharge), infection rate of treatment room the patient was treated in vs. average infection rate for other rooms, number of non-essential people in treatment room vs. average for similar cases, time and/or thoroughness spent on terminal cleaning of treatment room prior to the medical procedure, number of times a non-sterile door was opened during the medical procedure and/or any violations of a sterile field or back table that occurred during the medical procedure. All of the information can be analyzed to determine steps that can be taken in the future to minimize possibilities of readmission of the patient.

The analyzed data can also be used for tracking and improving medical procedures. For example, the following can be observed and recorded: usage and duration of use of the medical devices, personnel using the medical devices, number of sponges and/or needles used during the medical procedure (e.g., to ensure none are lost during the medical procedure), camera position for being minimally invasive during a particular medical procedure, registration and confirmation of implant sizes, anatomical placement of ports (e.g., trocars, scopes and incisions), hand placement of staff and physicians per procedure type, surgical techniques, wasted movements, idle personnel time, handling of instruments (e.g., when and by whom), time and duration of usage of any cutting or RF instrument, estimates on the volume of blood loss or fluid use, time of use of any disposable instrument, and time of activation of any device (e.g., activation of light source). Moreover, it is contemplated that algorithms can be used to identify the personnel 400 entering and exiting the room 10 along with the function of the personnel 400 entering and exiting the room 10 during a particular procedure. Such collected data can be used to develop plans for improving medical procedures. Such information (e.g., observation of number of devices (for example, sponges or needles) used in a procedure or critical procedural steps of a procedure) could prompt notification (e.g., by video or audio alerts) for corrective action that needs to be taken if important devices or steps are skipped or missed.

For all of the image recognition techniques outlined above (e.g., facial and/or other features as outlined above and device recognition), it is contemplated that a database of information needed to recognize the item or person in the image could be stored locally (e.g., in a memory of the computer system 48, 399) or externally. For example, the database of information can be stored externally and obtainable through the Internet or other type of wide area network (WAN), a local area network (LAN), a corporate intranet, any other type of network, a combination of such networks, or can be stored in cloud storage retrievable through a network interface of the computer system 48, 399. Information can be saved in the database of information by saving images into the database of information through any means (e.g., a web application or a mobile application) and associating names (e.g., name of person) or other information (e.g., type of device) with each particular image.

The analysis of video and/or images of the room 10 can be used for recognizing specific conditions of the room 10 and triggering or taking further action within the room depending on the specific conditions. For example, it is contemplated that the cameras 320 could review the rooms 10, and if it determined that no personnel 400 are in the room 10 (and possibly the additional determination that the time of day is outside normal utilization hours for the room 10) the computer system could trigger an ultraviolet room sterilization system 700 to eliminate pathogens in the room 10. If is further contemplated that the computer system 48, 399 could automatically turn off the ultraviolet room sterilization system 700 if the cameras 320 determine the presence of personnel 400 in the room 10 (e.g., personnel 400 entering the room) unless the computer system 48, 399 is programmed to determine if the personnel 400 is wearing protection gear (e.g., a special suit having a recognizable code or a particular type of reflectivity that can be visually determined) that protects the personnel 400 for ultraviolet light. It is contemplated that the system could take other action upon determination that personnel 400 are in or not in the room 10. For example, devices could be automatically turned on or off depending on whether there are personnel 400 in the room 10 or not in the room 10.

In the illustrated example, one or more of the cameras 320 (e.g., the room cameras) could capture video or images outside of the visible spectrum and the computer system 48, 399 could take action depending on the analysis of the video or images outside of the visible spectrum. For example, the cameras 320 could be infrared cameras that turn off equipment or provide notification that equipment is too hot for its intended purpose. Therefore, the equipment could be replaced before the equipment malfunctions. The cameras 320 could also be a hyperspectral imaging camera or a multispectral imaging camera. The hyperspectral imaging camera or the multispectral imaging camera could also sense light waves outside of the visible spectrum. The hyperspectral imaging camera or the multispectral imaging camera could provide video or images to the computer system 48, 399 to allow the computer system 48, 399 to notify the personnel 400 of certain conditions or take automatic action under certain conditions. For example, the computer system 48, 399 could alert the personnel 400 if the hyperspectral imaging camera or the multispectral imaging camera detect waste anesthesia gases venting into the room 10 instead of into a waste anesthesia gas disposal system. In another example, the computer system 48, 399 could alert the personnel 400 if the hyperspectral imaging camera or the multispectral imaging camera detect an increased volume of contaminants (e.g., dust or other particular matter) venting into the room 10 through the HVAC system.

The illustrated room 10 can also include one or more microphones 800 to receive audio in the room 10 for analysis by the computer system 48, 399. The microphone 800 can be fixed within the room 10 or can be portable and be wired or wireless connected to the computer system 48, 399. For example, it is contemplated that the microphone 800 could be worn by the personnel 400 (e.g., surgeon) or could be located in any of the devices. The computer system 48, 399 could analyze the audio received by the microphone 800. For example, the computer system 48, 399 could monitor the sounds from the medical equipment 16 for alarms or other telltale sounds that the equipment is not working properly (e.g., a high-pitched whine indicating a clogged air intake filter) and alert the personnel 400 in the room 10 or outside of the room 10 if an alarm count exceeds a preset number for the procedure in the room 10. The alert could be audio within the room, audio to personnel 400 outside the room, turning down music within the room, dimming or flashing lights in the room, placing text or other indicators on monitors or any other method of alerting personnel of issues. The computer system 48, 399 could monitor instructions from one of the personnel 400 in the room 10 (e.g., a doctor) and provide an audio or visual alert (e.g., on a monitor) if a discrepancy is detected between the instruction and the response by reviewing the audio response or by analyzing the video or images from the cameras 320 for the non-verbal action taken from the instructions. The computer system 48, 399 could monitor communications of the personnel 400 in the room 10 (e.g., a doctor) and automatically reduce the volume level of music playing in the room 10 under certain conditions (e.g., during prolonged verbal communications between the personnel 400 or when elevated levels of stress in the voices of the personnel 400 is detected). In addition to or as an alternative to reducing the volume level of music playing in the room 10 under the certain conditions, additional personnel 400 could be automatically called to the room 10. The audio recorded by the microphones 800 can be saved on the computer system 48, 399 or in the patient's record for later analysis (e.g., analysis to the audio to make correlations between interruption frequency (from, for example, equipment alarms, phone calls, etc.) and post-operative recovery issues so that potential conclusions can be drawn for improvement in patient safety.

In the illustrated embodiments as outlined above, instructions are given to personnel for many reasons. For example, instructions can be given to personnel in order to match actual attributes of the surgical devices with desired attributes of the surgical devices. It is contemplated that augmented reality system can be used to provide the instructions to the personnel in order to allow them to match the actual attributes with the desired attributes. An example of an augmented reality system that could be used is the Microsoft HoloLens as sold by Microsoft Corporation of Redmond, WA. The augmented reality system can be worn by the personnel to show exactly where the surgical devices should be positioned.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. A method of sterilizing an operating room comprising, at a computing system:
   capturing a first image of the operating room by at least one camera;
   determining that no people are present in the operating room based on analysis of the first image; and
   in response to determining that no people are present in the operating room, controlling an ultraviolet room sterilization system to sterilize at least a portion of the operating room.

2. The method of claim 1, wherein determining that no people are present in the operating room comprises determining that the first image was captured outside of regular utilization hours for the operating room.

3. The method of claim 1, wherein the at least one camera comprises a wide angle camera or a 360-degree camera.

4. The method of claim 1, wherein the at least one camera comprises a visible light camera or an infrared light camera.

5. The method of claim 1, wherein the at least one camera comprises a camera fixed to a wall or ceiling of the operating room.

6. The method of claim 1, comprising:
   capturing a second image of the operating room, wherein the second image is captured after the first image; and
   determining that at least one person is present in the operating room based on analysis of the second image.

7. The method of claim 6, comprising:
   in response to determining that at least one person is present in the operating room, deactivating the ultraviolet room sterilization system.

8. The method of claim 6, comprising:
  determining that the at least one person is not wearing protective gear based on analysis of the second image; and
  in response to determining that the at least one person is not wearing protective gear, deactivating the ultraviolet room sterilization system.

9. The method of claim 6, comprising:
  determining that the at least one person is wearing protective gear based on analysis of the second image; and
  in response to determining that the at least one person is wearing protective gear, continuing to control the ultraviolet room sterilization system to sterilize at least a portion of the operating room.

10. The method of claim 9, wherein protective gear comprises a suit configured to protect a wearer from ultraviolet light.

11. The method of claim 10, wherein the suit comprises a visual marker configured to be recognized by the at least one camera.

12. The method of claim 11, wherein the visual marker comprises a code.

13. The method of claim 11, wherein the visual marker comprises a reflective pattern.

14. A system for sterilizing an operating room, the system comprising at least one camera, wherein the system comprises one or more processors, memory, and software stored in the memory and comprising instructions for execution by the one or more processors for:
  determining that no people are present in the operating room based on analysis of a first image captured by the at least one camera; and
  in response to determining that no people are present in the operating room, controlling an ultraviolet room sterilization system to sterilize at least a portion of the operating room.

15. The system of claim 14, wherein determining that no people are present in the operating room comprises determining that the first image was captured outside of regular utilization hours for the operating room.

16. The system of claim 14, wherein the at least one camera comprises a wide angle camera or a 360-degree camera.

17. The system of claim 14, wherein the at least one camera comprises a visible light camera or an infrared camera.

18. The system of claim 14, wherein the at least one camera comprises a camera fixed to a wall or ceiling of the operating room.

19. The system of claim 14, wherein the system comprises the ultraviolet room sterilization system.

20. The system of claim 14, wherein the software includes instructions for:
  determining that at least one person is present in the operating room based on analysis of a second image captured by the at least one camera, wherein the second image is captured after the first image.

21. The system of claim 20, wherein the software includes instructions for:
  in response to determining that at least one person is present in the operating room, deactivating the ultraviolet room sterilization system.

22. The system of claim 20, wherein the software includes instructions for:
  determining that the at least one person is not wearing protective gear based on analysis of the second image; and
  in response to determining that the at least one person is not wearing protective gear, deactivating the ultraviolet room sterilization system.

23. The system of claim 20, wherein the software includes instructions for:
  determining that the at least one person is wearing protective gear based on analysis of the second image; and
  in response to determining that the at least one person is wearing protective gear, continuing to control the ultraviolet room sterilization system to sterilize at least a portion of the operating room.

24. The system of claim 23, wherein protective gear comprises a suit configured to protect a wearer from ultraviolet light.

25. The system of claim 24, wherein the suit comprises a visual marker configured to be recognized by the at least one camera.

26. The system of claim 25, wherein the visual marker comprises a code.

27. The system of claim 25, wherein the visual marker comprises a reflective pattern.

* * * * *